(12) United States Patent
Williams et al.

(10) Patent No.: US 8,748,168 B2
(45) Date of Patent: Jun. 10, 2014

(54) **STRAINS OF *E. COLI* FOR PLASMID DNA PRODUCTION**

(75) Inventors: James A. Williams, Lincoln, NE (US); Clague P. Hodgson, Omaha, NE (US)

(73) Assignee: Nature Technology Corp., Lincoln, NE (US)

( * ) Notice: Subject to any disclaimer, the term of this patent is extended or adjusted under 35 U.S.C. 154(b) by 43 days.

(21) Appl. No.: 11/573,756

(22) PCT Filed: Aug. 15, 2005

(86) PCT No.: PCT/US2005/028870
§ 371 (c)(1),
(2), (4) Date: Mar. 17, 2007

(87) PCT Pub. No.: WO2006/026125
PCT Pub. Date: Mar. 9, 2006

(65) Prior Publication Data
US 2007/0249042 A1     Oct. 25, 2007

Related U.S. Application Data

(60) Provisional application No. 60/602,074, filed on Aug. 16, 2004.

(51) Int. Cl.
*C12N 15/00* (2006.01)

(52) U.S. Cl.
USPC ..................................................... 435/320.1

(58) Field of Classification Search
USPC ..................................................... 435/320.1
See application file for complete search history.

(56) References Cited

U.S. PATENT DOCUMENTS

| | | | |
|---|---|---|---|
| 4,755,464 | A | 7/1988 | MacPhee et al. |
| 5,591,064 | A | 1/1997 | Spears, Jr. |
| 6,011,148 | A | 1/2000 | Bussey et al. |
| 6,214,586 | B1 | 4/2001 | McNeilly |
| 6,242,220 | B1 * | 6/2001 | Wahle et al. .............. 435/91.1 |
| 6,258,560 | B1 | 7/2001 | Leung et al. |
| 6,287,762 | B1 | 9/2001 | Crouzet et al. |
| 6,455,287 | B1 | 9/2002 | Jem |
| 6,730,781 | B1 | 5/2004 | Wils et al. |
| 2001/0034435 | A1 | 10/2001 | NoChumson et al. |
| 2002/0142384 | A1 | 10/2002 | Sanders |
| 2002/0151048 | A1 | 10/2002 | Lander et al. |
| 2002/0197637 | A1 | 12/2002 | Willson, III et al. |
| 2003/0092885 | A1 | 5/2003 | Zhou et al. |
| 2003/0125522 | A1 | 7/2003 | Kim |
| 2004/0014197 | A1 | 1/2004 | Huisman et al. |

FOREIGN PATENT DOCUMENTS

| | | | |
|---|---|---|---|
| WO | 9213963 | A1 | 8/1992 |
| WO | 0028048 | A1 | 5/2000 |
| WO | 0129209 | A1 | 4/2001 |
| WO | 03046177 | A1 | 6/2003 |

OTHER PUBLICATIONS

Birnboim, A Rapid Alkaline Extraction Procedure for Screening Recombinant Plasmid DNA, 1979, Nucleic Acids Research, vol. 7, No. 6, pp. 1513-1523, Information Retrieval Limimted.
Diogo et al, Purification of a Cystic Fibrosis Plasmid Vector for Gene Therapy Using Hydrophobic Interaction Chromatography, 2000, Biotechnology and Bioengineering, vol. 68, No. 5, pp. 576-583.
Lemmens et al, Supercoiled Plasmid DNA: Selective Purification by Thiophilic/Aromatic Adsorption, 2003, Journal Chromatography B, vol. 784, pp. 291-300, Elsevier Science B.V.
U.S. Department of Health and Human Services, Food and Drug Administration, Center for Biologics Evaluation and Research, Mar. 1998, Guidance for Industry: Guidance for Human Somatic Cell Therapy and Gene Therapy.
U.S. Department of Health and Human Services, Food and Drug Administration, Center for Biologics Evaluation and Research, Dec. 1996, Points to Consider on Plasmid DNA Vaccines for Preventative Infectious Disease Indications.
U.S. Department of Health and Human Services, Food and Drug Administration, Center for Biologics Evaluation and Research, May 1993, Points to Consider in the Characterization of Cell Lines Used to Produce Biologics.
Isfort, Enzymatic Purification of Plasmid DNA, 1992, BioTechniques, vol. 12, pp. 798-804.
Sancar et al, Simple Method for Identification of Plasmid-Coded Proteins, Jan. 1979, Journal Bacteriology, vol. 137, pp. 692-693.
Cooke et al, Purification of Essentially RNA Free Plasmid DNA Using a Modified *Escherichia coli* Host Strain Expressing Ribonuclease A, 2001, Journal of Biotechnology, vol. 85, pp. 297-304, Elsevier Science B.V.
Cooke et al, A Modified *Escherichia coli* Protein Production Strain Expressing Staphylococcal Nuclease Capable of Auto-Hydrolysing Host Nucleic Acid, 2003, Journal of Biotechnology, vol. 101, pp. 229-239, Elsevier Science B.V.

(Continued)

*Primary Examiner* — Michael C. Wilson

(57) ABSTRACT

A general method and strains of bacteria are described, by means of which it is possible to dramatically purify plasmid DNA with respect to genomic DNA, and RNA. In one preferred embodiment, lysis and nuclease removal of host nucleic acids is an integral component of the fermentation/harvest process, and as such, achieves increased yield and purity with simplified downstream purification and reduced waste streams, thus reducing production costs.

2 Claims, 19 Drawing Sheets

(56) References Cited

OTHER PUBLICATIONS

Figure 1:
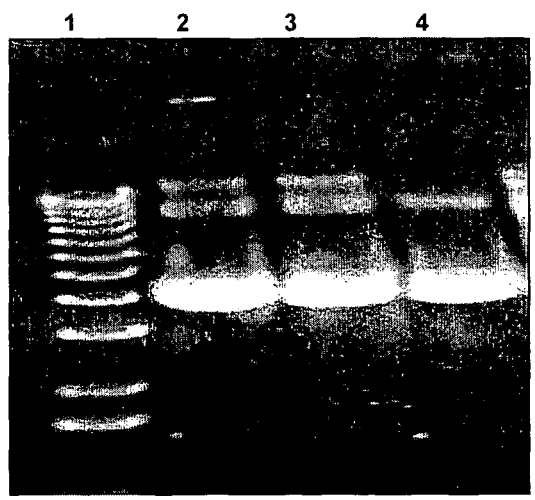

Boyton et al, Reduction of Cell Lysate Viscosity During Processing of Poly(3-Hydroxyalkanoates) by Chromosomal Integration of the Staphylococcal Nuclease Gene in *Pseudomonas putida*, Apr. 1999, Applied and Environmental Microbiology, vol. 65, pp. 1524-1529, American Society for Microbiology.

Kelly, Perspectives on Plasmid-Based Gene Therapy: Challenges for the Product and the Process, 2003, Biotechnol Appl Biochem, vol. 37, pp. 219-223, Portland Press Ltd.

Young, Bacteriophage Lysis: Mechanism and Regulation, Sep. 1992, Microbiological Reviews, vol. 56, pp. 430-481, American Society for Microbiology.

Sayers et al, Properties of Overexpressed Phage T5 D15 Exonuclease, 1990, The Journal of Biological Chemistry, vol. 265, No. 30, pp. 18311-18317, The American Society for Biochemistry and Molecular Biology, Inc.

Sayers et al, Identification and Eradication of a Denatured DNA Isolated During Alkaline Lysis-Based Plasmid Purification Procedures, 1996, Analytical Biochemistry, vol. 241, pp. 186-189, Article No. 0397.

Lu et al, Histidine Patch Thioredoxins, 1996, The Journal of Biological Chemistry, vol. 271, No. 9, pp. 5059-5065, The American Society for Biochemistry and Molecular Biology, Inc.

Park et al, Effects of Novel Peptides Derived From the Acidic Tail of Synuclein (ATS) on the Aggregation and Stability of Fusion Proteins, 2004, Protein Engineering, Design & Selection, vol. 17, No. 3, pp. 251-260, Oxford University Press.

De Marco et al, Recombinant Proteins Fused to Thermostable Partners Can Be Purified by Heat Incubation, 2004, Journal of Biotechnology, vol. 107, pp. 125-133, Elsevier B.V.

Makrides, Strategies for Achieving High-Level Expression of Genes in *Escherichia coli*, Sep. 1996, Microbiological Reviews, vol. 60, No. 3, pp. 512-538, American Society for Microbiology.

Choi et al, Secretory and Extracellular Production of Recombinant Proteins Using *Escherichia coli*, 2004, Appl Microbiol Biotechnol, vol. 64, pp. 625-635.

Harvey et al, Anchored Periplasmic Expression, A Versatile Technology for the Isolation of High-Affinity Antibodies from *Escherichia coli*-Expressed Libraries, 2004, Proc Natl Acad Sci, vol. 101, No. 25, pp. 9193-9198.

Collen et al, Genetically Engineered Peptide Fusions for Improved Protein Partitioning in Aqueous Two-Phase Systems, Effect of Fusion Localization on Endoglucanase I of *Trichoderma reesei*, 2001, Journal of Chromatography A, vol. 910, pp. 275-284, Elsevier Science B.V.

Zhao et al, Directed Evolution of Enzymes and Pathways for Industrial Biocatalysis, 2002, Current Opinions in Biotechnology, vol. 13, pp. 104-110, Elsevier Science B.V.

Ness et al, Synthetic Shuffling Expands Functional Protein Diversity by Allowing Amino Acids to Recombine Independently, Dec. 2002, Nature Biotechnology, vol. 20, pp. 1251-1255.

Kurtzman et al, Advances in Directed Protein Evolution by Recursive Genetic Recombination: Applications to Therapeutic Proteins, 2001, Current Opinions in Biotechnology, vol. 12, pp. 361-370, Elsevier Science Ltd.

Wang et al, Holins: The Protein Clocks of Bacteriophage Infections, 2000, Annu Rev Microbiol, vol. 54, pp. 799-825.

Bernhardt et al, Breaking Free: "Protein Antibiotics" and Phage Lysis, 2002, Research in Microbiology, vol. 153, pp. 493-501.

Witte et al, Biochemical Characterization of _X174-Protein-E-Mediated Lysis of *Escherichia coli*, 1989, Eur J. Biochem, vol. 180, pp. 393-398.

Young et al, Phages Will Out: Strategies of Host Cell Lysis, 2000, Trends in Microbiology, vol. 8, No. 3, pp. 120-128, Elsevier Science Ltd.

Jalava et al, Bacterial Ghosts as Carrier and Targeting Systems for Mucosal Antigen Delivery, 2003, Expert Rev Vaccines, vol. 2, No. 1, pp. 45-51.

Murphy, Use of Bacteriophage _ Recombination Functions to Promote Gene Replacement in *Escherichia coli*, 1998, Journal of Bacteriology, vol. 180, No. 8, pp. 2063-2071, American Society for Microbiology.

Datsenko et al, One-Step Inactivation of Chromosomal Genes in *Escherichia coli* K-12 Using PCR Products, 2000, Proc Natl Acad Sci USA, vol. 97, No. 12, pp. 6640-6645.

Carnes, Fermentation Design for the Manufacture of Therapeutic Plasmid DNA, Oct. 2005, BioProcess International, vol. 3, No. 9, pp. 36-42.

Williams et al, Expression of Foreign Proteins in *E. coli* Using Plasmid Vectors and Purification of Specific Polyclonal Antibodies, 1995, DNA Cloning 2: A Practical Approach, 2nd Edition, Edited by Glover and Hames, Chapter 2, pp. 15-58, Oxford University Press.

McCormick et al, S•Tag: A Multipurpose Fusion Peptide for Recombinant Proteins, May 1994, InNovations, vol. 1, pp. 4-7.

Jechlinger et al, Altered Temperature Induction Sensitivity of the Lambda PR/cI857 System for Controlled Gene E Expression in *Escherichia coli*, 1999, FEMS Microbiology Letters, vol. 173, pp. 347-352, Federation of European Microbiological Societies.

Jechlinger et al, Cold-Sensitive E-Lysis Systems, 1998, GENE: An International Journal on Genes and Genomes, vol. 218, pp. 1-7.

\* cited by examiner

5'- *Sap* I site N^GGG^NNNNNNNNNNN - 3'
                    tag   -   primer

STRAINS OF *E. COLI* FOR PLASMID DNA PRODUCTION

CROSS-REFERENCE TO RELATED APPLICATION

This application claims the benefit of U.S. provisional application Ser. No. 60/602,074 filed 16 Aug. 2004.

STATEMENT REGARDING FEDERALLY SPONSORED RESEARCH OR DEVELOPMENT

This invention was made in part with government support under Grant No. 1 R43 GM072141-01, awarded by the National Institutes of Health. The government has certain rights in this invention.

FIELD OF THE INVENTION

The present invention relates to the production of covalently closed circular (ccc) recombinant DNA molecules such as plasmids, cosmids, bacterial artificial chromosomes (BACs), bacteriophages, viral vectors and hybrids thereof, and more particularly is a method for purification of the said DNA molecules away from contaminating nucleic acid molecules associated with the fermentation.

BACKGROUND OF THE INVENTION

The present invention relates to the production of covalently closed circular (ccc) recombinant DNA molecules. Such molecules are useful in biotechnology, transgenic organisms, gene therapy, therapeutic vaccination, agriculture and DNA vaccines.

With the invention in mind, a search of the prior art was conducted. *E. coli* plasmids have long been the single most important source of recombinant DNA molecules used by researchers and by industry. Today, plasmid DNA is becoming increasingly important as the next generation of biotechnology products (gene medicines and DNA vaccines) make their way into clinical trials, and eventually into the pharmaceutical marketplace. Plasmid DNA vaccines may find application as preventive vaccines for viral, bacterial, or parasitic diseases; immunizing agents for the preparation of hyper immune globulin products; therapeutic vaccines for infectious diseases; or as cancer vaccines.

The basic methods for obtaining plasmids (by bacterial fermentation), and for their purification by the alkaline lysis method are well-known (Birnboim, H C, Doly J. 1979 *Nucleic Acids Res.* 7: 1513-1523). Initially, the fermented bacterial cell paste is resuspended and lysed (using a combination of sodium hydroxide and sodium dodecylsulfate), after which the solution is neutralized by the addition of acidic salt (e.g., potassium acetate), which precipitates the bacterial DNA and the majority of cell debris. The bulk of super-coiled plasmid DNA remains in solution, along with contaminating bacterial RNA, DNA and proteins, as well as *E. coli* endotoxin (lipopolysaccharide, or LPS).

Alternatively lysis using heat/lysozyme treatment in the presence of nonionic detergent has been used to release intact plasmid DNA. Cells can also be lysed, and nucleic acids released, using high pressure exposure to supercritical fluids or by treatment with organic solvents, or detergents.

These lysis methods release cell impurities, which then require purification steps to remove. As well, the alkaline lysis or heat denaturation cell lysis methodologies currently utilized in plasmid DNA manufacture are costly, inefficient, and create large toxic waste-streams. Alternative, cost effective lysis methods have not been developed.

The soluble fraction is then separated by filtration and subjected to a variety of purification steps, which may include: RNase digestion; chromatography (ion exchange gel filtration, hydroxyapatite, gel filtration, hydrophobic interaction, reverse phase, HPLC, etc.); diafiltration; organic extraction, selective precipitation, etc.

Exemplary downstream plasmid purification processes after lysis described in the art reduce genomic DNA levels to 0.01-1% or less. The following processes described in the art are not an exhaustive list, and include the specified genomic DNA reduction steps: 0.01% genomic with hydroxyapatite (Wils P, and Ollivier, M. 2004 U.S. Pat. No. 6,730,781), 0.05% genomic with hydrophobic interaction chromatography (Nochumson S, Durland R, Yu-Speight A, Welp J, Wu K, and Hayes R. 2001 US Patent Application 2001/0034435; Diogo M M, Querioz J A, Monteiro, G A, Martins S A M, Ferreira, G N M, and Prazeres D M F. 2000 *Biotech Bioeng* 68:576-583), 1% genomic with ammonium sulfate precipitation (McNeilly D S. 2001 U.S. Pat. No. 6,214,586), 0.2% genomic with size exclusion chromatography (Lemmens R, Olsson U, Nyhammar T, and Stadler J. 2003. *J Chromatography B* 784:291-300), <1% genomic with Tangential flow ultrafiltration (Bussey L B, Adamson R, and Atchley A. 2000 U.S. Pat. No. 6,011,148), <1% genomic with differential polyethylene glycol precipitation (Marquet M, Horn N, Meek J, and Budahazi G. 1996 U.S. Pat. No. 5,591,064), CTAB precipitation and gryolite LRA absorption (Lander R J, Winters M A, and Meacle F J. 2002 US Patent Application 2002/0151048), 0.1% genomic with triple helix chromatography (Crouzet J, Scherman D, and Wils P. 2001 U.S. Pat. No. 6,287,762).

The introduction of plasmid DNA into humans presents some special considerations and challenges, which have been addressed in FDA regulatory guidance, including Points to consider on plasmid DNA vaccines for preventive infectious disease indications (Food and Drug Administration, Center for Biologics Evaluation and Research. 1996 Points to consider on plasmid DNA vaccines for preventive infectious disease indications DOCKET NO. 96N-0400, and Food and Drug Administration, Center for Biologics Evaluation and Research. 1998 Guidance for industry: Guidance for human somatic cell therapy and gene therapy.). These documents indicate concerns about the various contaminating substances, and suggest tests that can be used to assess the levels of each contaminant. The guidance documents stop short, however, of suggesting maximum acceptable levels of contaminating RNA, DNA or proteins, as these are not known. However, the allowable limit for genomic DNA would be 0.00001% if the 100 pg genomic DNA/dose specification currently required by FDA guidelines for recombinant protein drugs (FDA. 1993 Points to consider in the characterization of cell lines used to produce biologics) were applied to a 1 mg DNA vaccine dose. This is several logs lower levels than standard large scale plasmid DNA preparations (0.01-5% genomic DNA) and cannot be attained using currently available cost effective manufacturing methodologies. New methods are needed to afford further reductions in genomic DNA.

Nucleic acids can be eliminated early in the process (e.g., by nuclease digestion), or later (e.g., by chromatographic separation). A relatively common practice, until recently, was the use of bovine pancreatic ribonuclease (RNase A) in the lysis buffer, to degrade RNA. Although it was reasonably effective in reducing the quantity and size of RNA, it also introduced the bovine-source RNase, which is undesirable from a regulatory standpoint, as it could be contaminated with prion agents, notably with the bovine spongiform encephalitis (BSE) agent. Indeed, there is a growing desire to perform fermentations and purifications of bacterial products (intended for human or animal use) entirely under animal product free (APF) conditions.

Presently, we know of no highly effective commercial enzymes for specifically degrading *E. coli* genomic DNA while leaving super-coiled plasmid intact ('plasmid-safe' nuclease). Occasionally, however, nucleases, such as the ATP-dependent Rec BCD exonuclease enzymes (Qiagen Large Construct Kit Handbook, June 2003; Wahle, S, Schorr J, and Weber M. 2001 U.S. Pat. No. 6,242,220; Isfort R J 1992 *BioTechniques* 12: 798-804) are added to partially purified plasmid DNA preparations. In a related approach, the crude plasmid preparation is heat treated to denature all non-circular DNA to single stranded form, then single stranded exonucleases such as SI nuclease, mung bean nuclease, P1 nuclease, T7 exonuclease, Bal31 nuclease, Exonuclease I, Exonuclease III, Exonuclease VII or Lambda Exonuclease (Hyman E D. 1992 World Patent Application 92/13963) is added. These DNase enzymes cannot be added directly to the lysis (as with RNase), because these enzymes are generally more fragile than RNase, and would be inactivated in an alkaline/SDS environment. Such approaches are therefore expensive and impractical for commercial scale plasmid manufacturing.

In order to overcome the obstacles that exist with adding purified nucleases to plasmid DNA preparations, alternative approaches have been developed that utilize endogenous nucleases to remove genomic DNA. Early methods induced general DNA damage (e.g. ultraviolet radiation in repair deficient hosts (Sancar A, Hack A M, and Rupp W D. 1979 *J Bacteriol.* 137: 692-693), or ionizing irradiation (MacPhee D G, Radford, A J, and Reanney D C. 1988 U.S. Pat. No. 4,755,464) in which plasmids survive due to a lower probability of damage (i.e. smaller target than the genome) relative to the chromosome; degradation, mediated by endogenous nucleases (e.g. RecBCD), proceeds from the DNA breakage sites in the genome. A more specific system that utilizes restriction endonucleases to cleave genomic DNA has been reported, wherein restriction endonuclease activity is controlled by a thermosensitive methylase. Shifting to the restrictive temperature inactivates the methylase, leading to cleavage of genomic DNA, and subsequent endogenous exonuclease digestion (Hanak, J, Alexis J, and Ward J M. 2001 World Patent Application WO 01/29209). However, the level of genomic reduction is modest with these methods, and plasmids would need to be engineered to lack the relevant restriction sites so this method does not have general utility.

Specialized *E. coli* strains have been developed, which express recombinant nucleases in the periplasmic space in order not to disrupt *E. coli* gene expression during cell growth. In one case bovine pancreatic RNase is directed to the periplasmic space by means of a secretion signal, Upon lysis, the RNase becomes mixed with the RNA, degrading it (Cooke G D, Cranenburgh R M, Hanak J A J, Dunnill P, Thatcher D R, Ward J M. 2001 A *J. Biotechnology* 85: 297-304). This system is utilized to reduce RNA levels during alkaline lysis. No reduction in genomic DNA is afforded by this method. Similar systems to overexpress periplasmic Staphylococcal nuclease (Cooke G D, Cranenburgh R M, Hanak J A J, Ward J M. 2003 *J. Biotechnology* 101: 229-239; Huisman G W, Luo L Z, and Peoples O P. 2004 US Patent Application 2004/0014197; Boynton Z L, Koon J L, Brennan E M, Clouart J D, Horowitz D M, Gerngross T U, and Huisman G W. 1999 *Pseudomonas putida. Appl. Environ. Microbiol.* 65:1524-1529), or endogenous *E. coli* EndA periplasmic nuclease (Leung W S, and Swartz J R. 2001 U.S. Pat. No. 6,258,560) have been developed, to reduce nucleic acid contamination of protein or other biomaterial preparations. These systems are not plasmid-safe, and require gentle protein purification processes and buffers for activity. The induction of plasmid-safe DNases in fermentation culture is discussed in theoretical context by Kelly 2003 (Kelly W J. 2003 *Biotechnol Appl Biochem* 37:219-223) but a methodology or nuclease is not specified.

Autolytic cell lines have been developed to facilitate protein production (Leung and Swartz, Supra, 2001). In this cell line, lysozyme is expressed by the cell in the cytoplasm, and released to the periplasm at the desired time by co-expression of a holin (membrane spanning peptide or protein) that creates a channel allowing leakage of lysozyme, and other cytoplasmic proteins, from the cytoplasm to the periplasm. Example lysozyme/holin combinations that can be utilized are known in the art. Some lysozyme/holin combinations are discussed in Young 1992 (Young R. 1992 *Microbiol. Molec. Reviews,* 56: 430-481) and included herein by reference. The phage lambda lysis proteins have been used in autolytic cell lines for the production of proteins (Leung and Swartz, Supra, 2001).

Autolysis conditions, as opposed to alkaline or heat lysis, do not selectively denature genomic DNA. The product of lysis is very viscous, creating processing problems. For protein production, non specific nucleases are added, or expressed periplasmically in the strain (e.g. endA nuclease Leung and Swartz, Supra, 2001; *Staphylococcus* nuclease; Cooke et al, Supra, 2003, Huisman et al, Supra, 2005, Boynton et al, Supra, 1999) to reduce viscosity after cell lysis. Such systems could not be utilized for plasmid production.

The purification processes utilized in plasmid DNA manufacture are costly, inefficient, and create large toxic waste streams. Residual genomic DNA levels greatly exceed currently acceptable standards for commercial products. These limitations place a cost and purity burden on commercialization of plasmid DNA production processes.

Even in view of the prior art, there remains a need for a cost effective method for genomic DNA reduction. As well, a simplified, less costly purification process which reduces the use of costly or toxic chemicals is needed.

DISCLOSURE OF THE INVENTION

The invention is a method for production of DNA, in which one or more genes encoding plasmid-safe nuclease(s) is inserted into the bacterial genome, and which are expressed as protein secreted into the periplasmic space. When a plasmid or DNA replicon is grown in the cells, the nuclease is reintroduced into the cytoplasm, eliminating nucleic acids other than the desired replicon, facilitating the purification of the replicon. In one preferred embodiment, the nuclease is a chimeric nuclease. In another preferred embodiment, the chimeric nuclease is a DNAse with at least a portion of an RNase enzyme as a fusion partner. Yet other preferred embodiments utilize a chimeric enzyme fusing phage T5 D15 exonuclease with RNaseA or RNaseS. In a preferred form of the method, the nuclease(s) are directed to the periplasmic space by means of a signal peptide or equivalent process, and the cells are autolysed such that the bacterial genomic DNA and/or RNA are digested and the DNA of the introduced replicon is not digested, thus facilitating the purification of the introduced replicon. In yet other preferred embodiments, the autolysis is achieved either through the use of phage lysis proteins expressed in the cells, or through the use of antibiotics. The invention includes strains of bacteria having at least one plasmid-safe nuclease, with or without a fusion partner, and a plasmid, the purification of which is facilitated by the plasmid-safe nuclease.

BRIEF SUMMARY OF THE INVENTION

It is a purpose and/or objective of the present invention to provide compositions of matter and a plasmid purification process. Another object of the invention is to provide a method to reduce nucleic acid impurities in purified plasmid DNA. Yet another object of the invention is to reduce production costs for plasmid DNA purification. Yet another objective and/or purpose of the invention is to reduce toxic waste steams in plasmid DNA purification. Another disclosure is improved plasmid production processes that, compared to processes defined in the art are improved by: increased quality of plasmid by reduced levels of nicked (open circular) or linearized versions of the plasmid; simplified production using robust production steps; simplified production through elimination of multiple production steps; reduced cost through elimination of multiple production steps; increased quality of plasmid by reduction of nucleic acid impurities after plasmid purification due to elimination of key contaminants prior to entry into downstream processing; improved regulatory compliance by elimination of genomic DNA from final plasmid preparations; improved regulatory compliance by elimination of animal product sourced materials such as ribonuclease A; and improved regulatory compliance by elimination of toxic waste streams.

Further objects and advantages of the invention will become apparent from a consideration of the drawings and ensuing description.

BRIEF DESCRIPTION OF THE DRAWING FIGURES

FIG. 1. Illustrates digestion of denatured plasmid and *E. coli* genomic DNA by T5 exonuclease.

Figure 2:
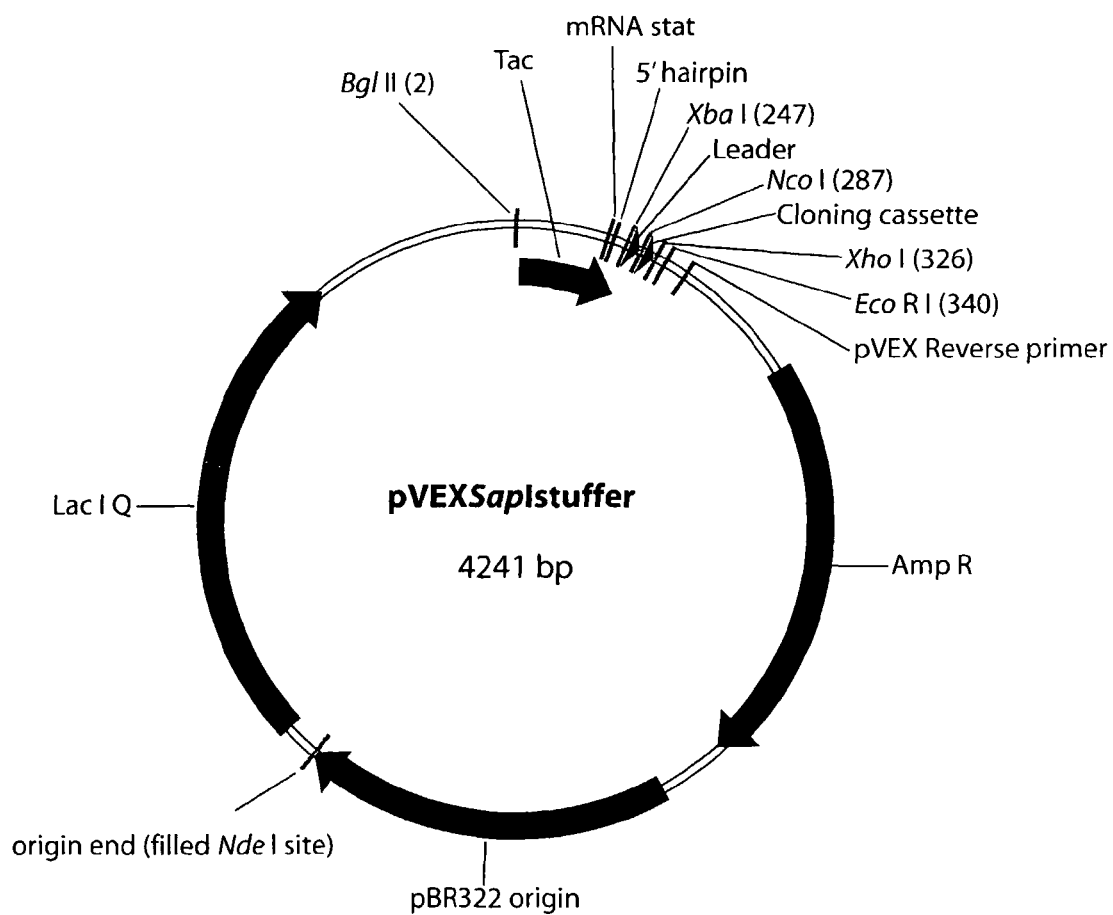

FIG. 2. shows the pVEXSapIstuffer vector.

Figure 3:
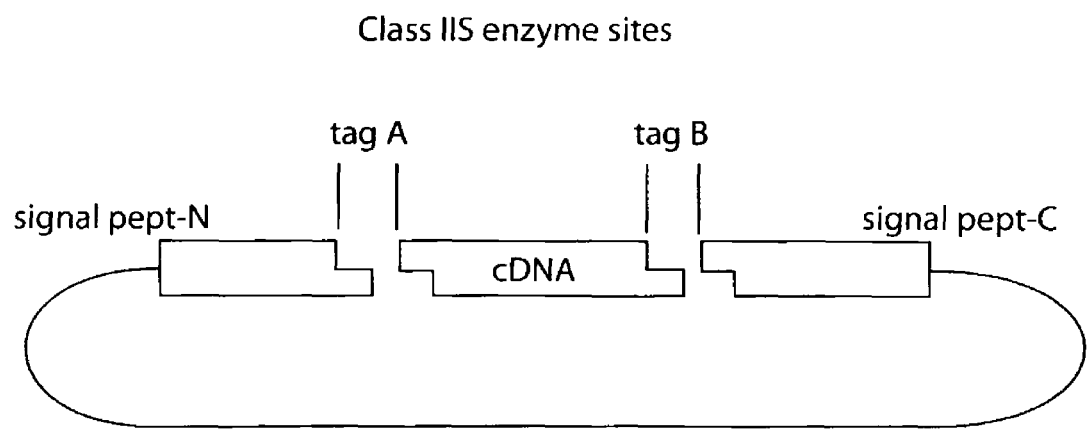

FIG. 3. reveals a method for directional amplification and cloning of cDNA sequences into pVEX vectors.

Figure 4:
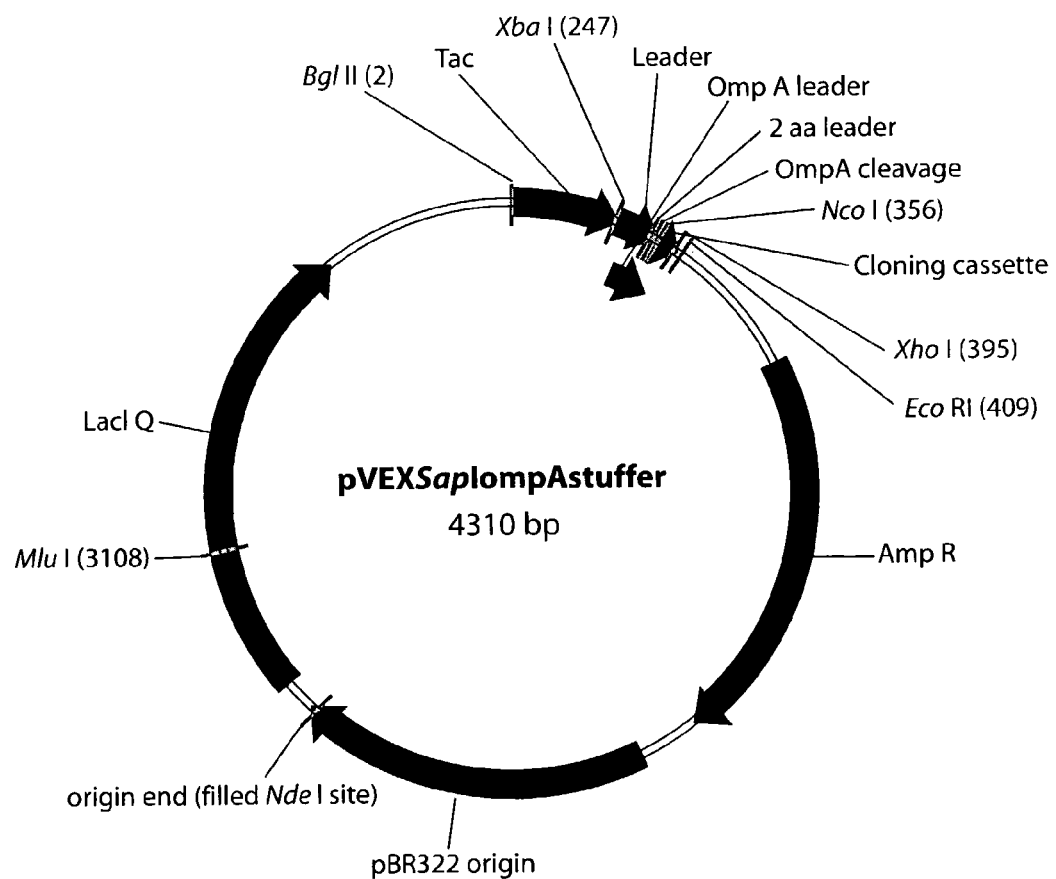

FIG. 4. illustrates the pVEXSapIOmpAStuffer vector.

Figure 5:
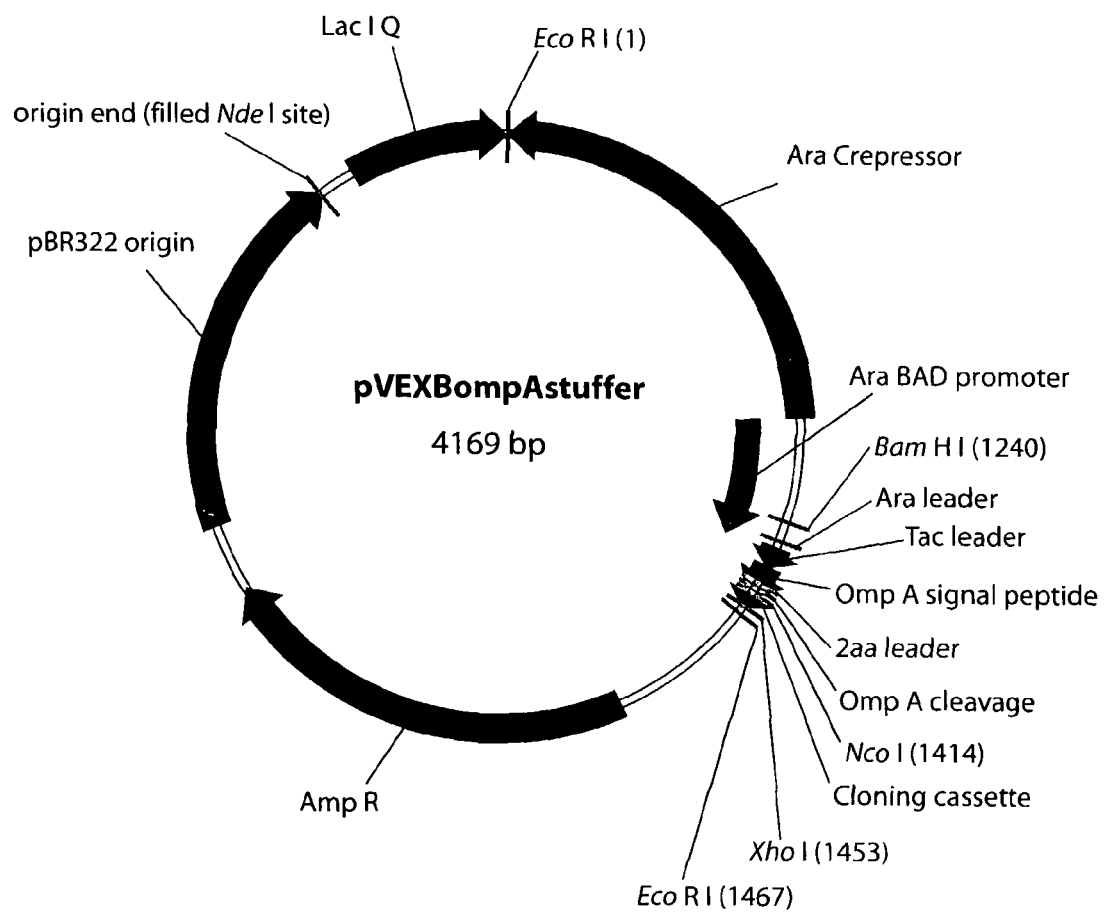

FIG. 5. shows the pVEXBSapIOmpAStuffer vector.

Figure 6:
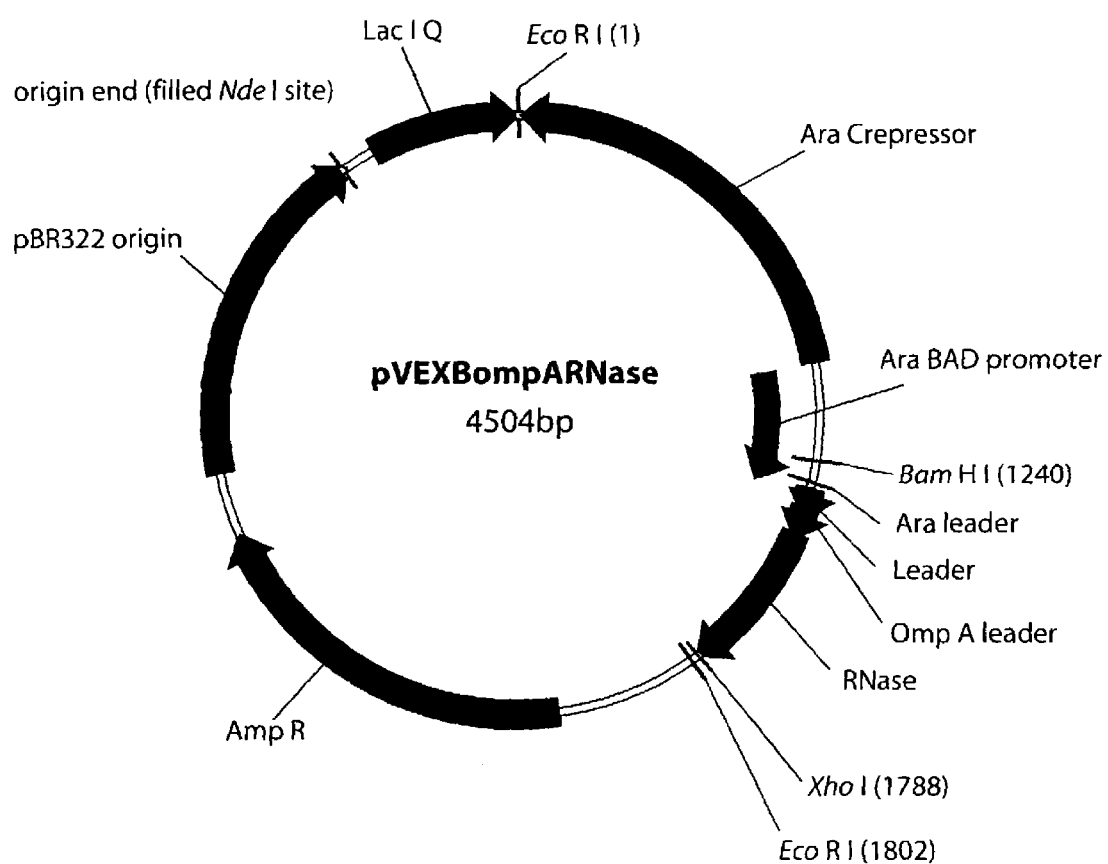

FIG. 6. reveals the pVEXBOmpARNase vector.

Figure 7:
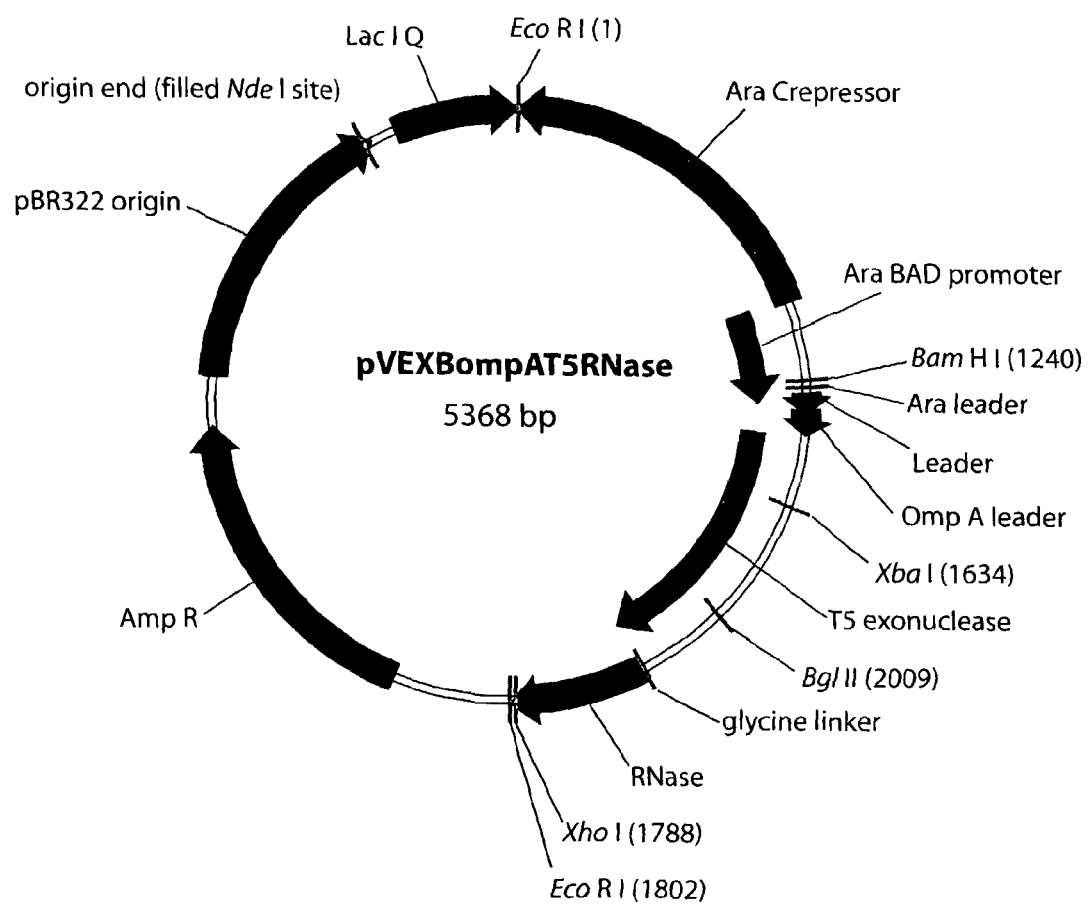

FIG. 7. illustrates the pVEXBOmpAT5RNase vector.

Figure 8:
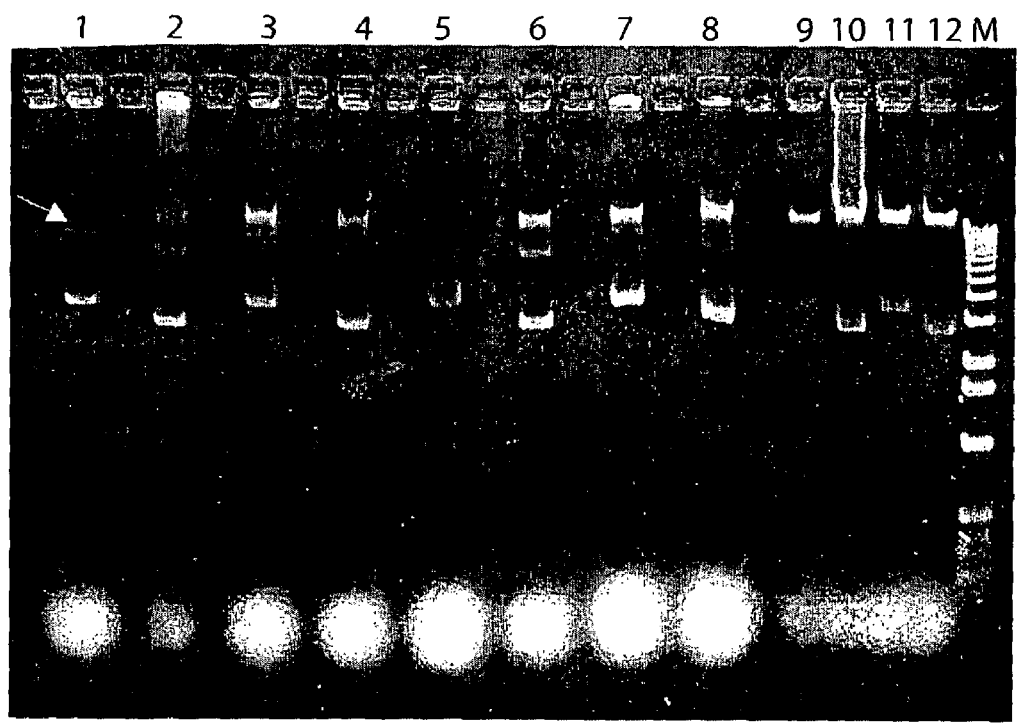

FIG. 8. shows T5RNase exonuclease removal of genomic DNA. A gel photo of plasmid DNA. preparations is shown, with and without the use of the preferred T5 exonuclease and RNase gene(s).

Figure 9:
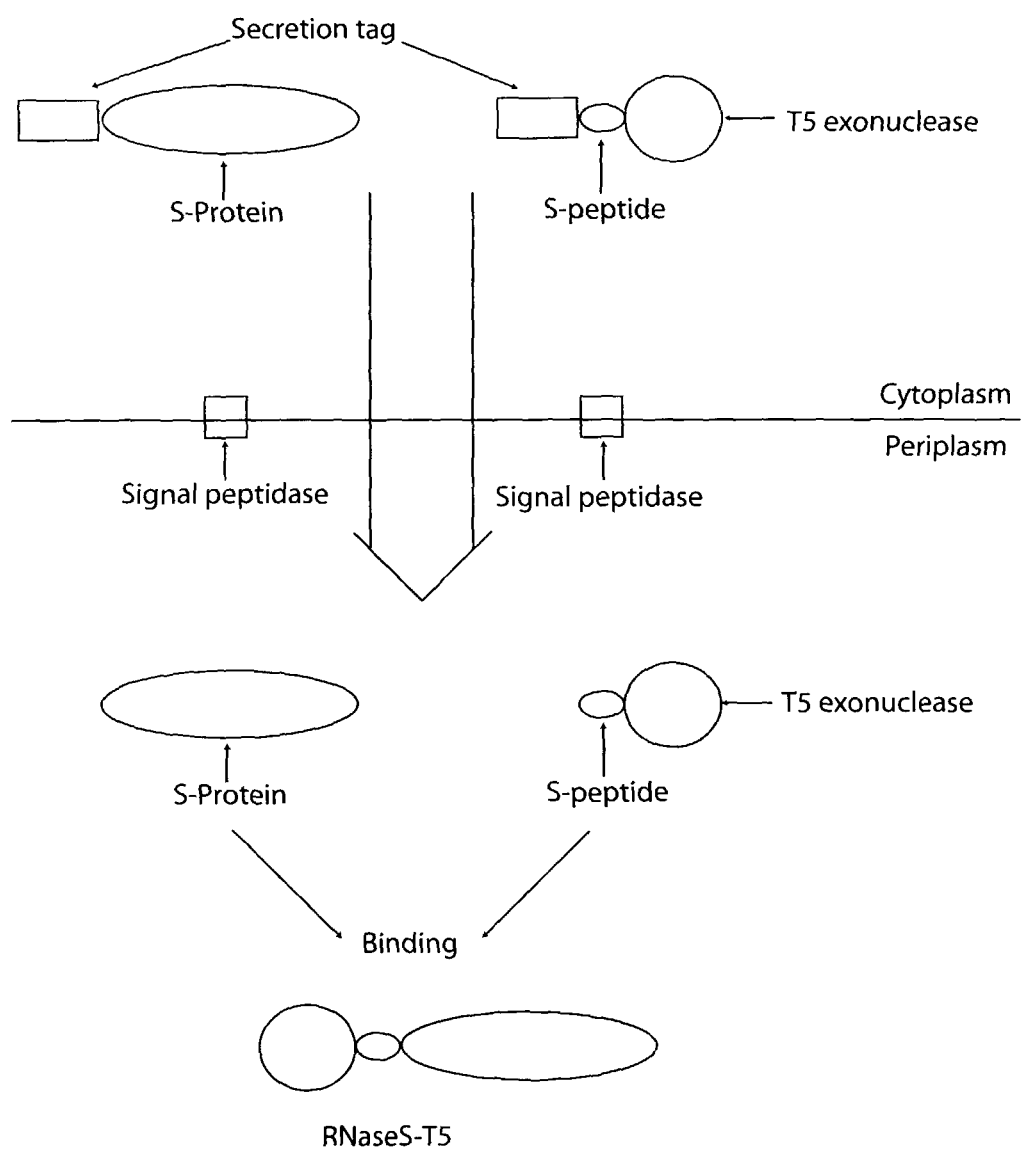

FIG. 9. illustrates the use of S-peptide and S-protein association to make the RNaseS-T5 chimera.

Figure 10:
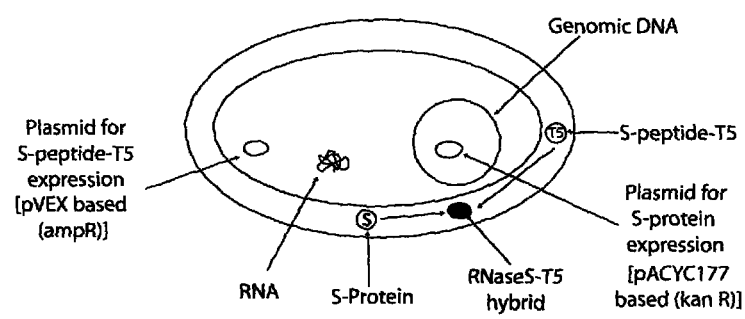
Figure 10:
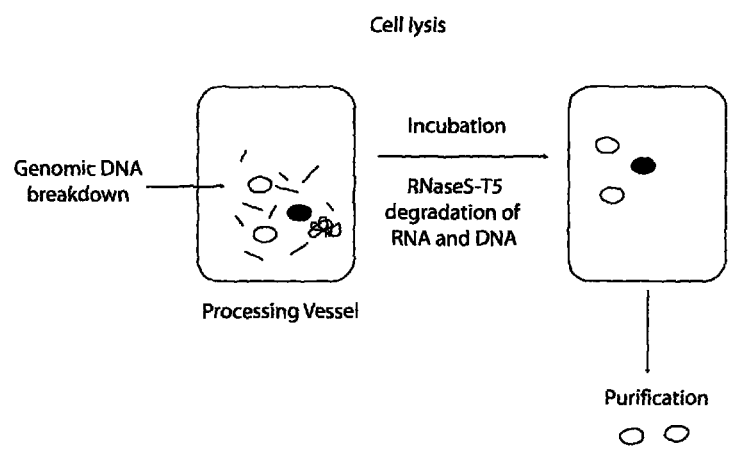

FIG. 10. demonstrates nucleic acid hydrolysis by a chimeric nuclease.

Figure 11:
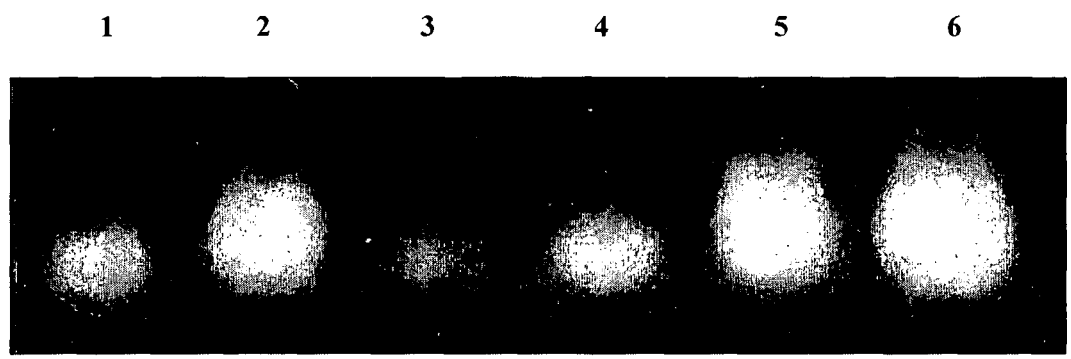

FIG. 11. shows RNA reduction with Speptide-T5+Sprotein and T5RNase constructs.

Figure 12:
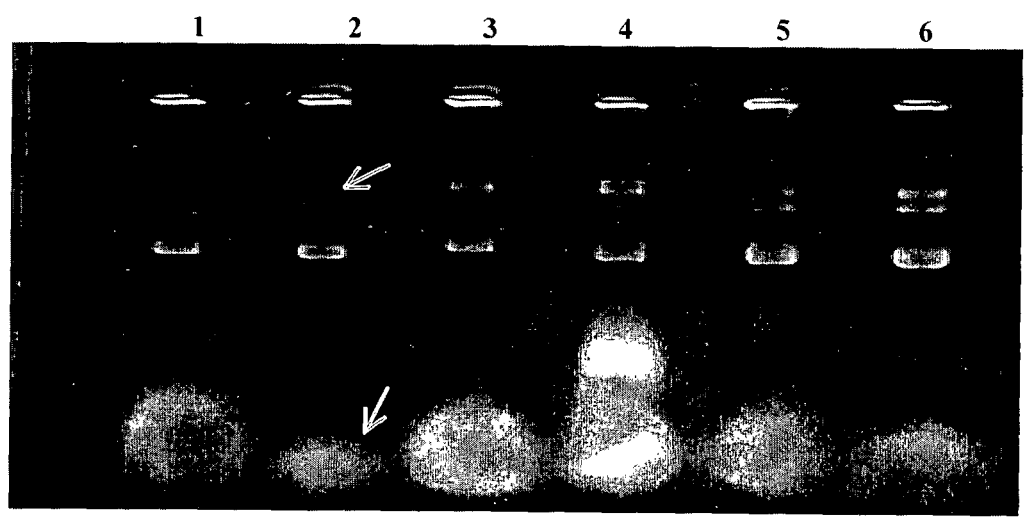

FIG. 12. reveals RNA and genomic DNA reduction with an Speptide-T5+Sprotein construct.

Figure 13:
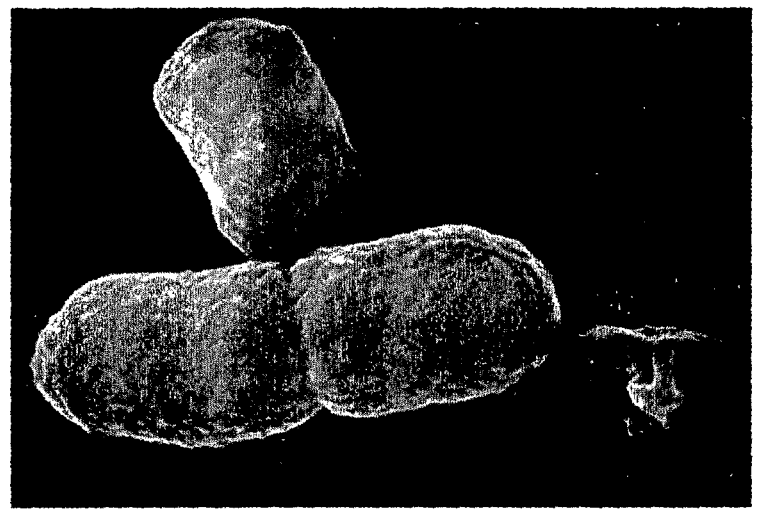

FIG. 13. illustrates release of *E. Coli* cytoplasmic contents through PhiX174 gene E pore.

Figure 14:
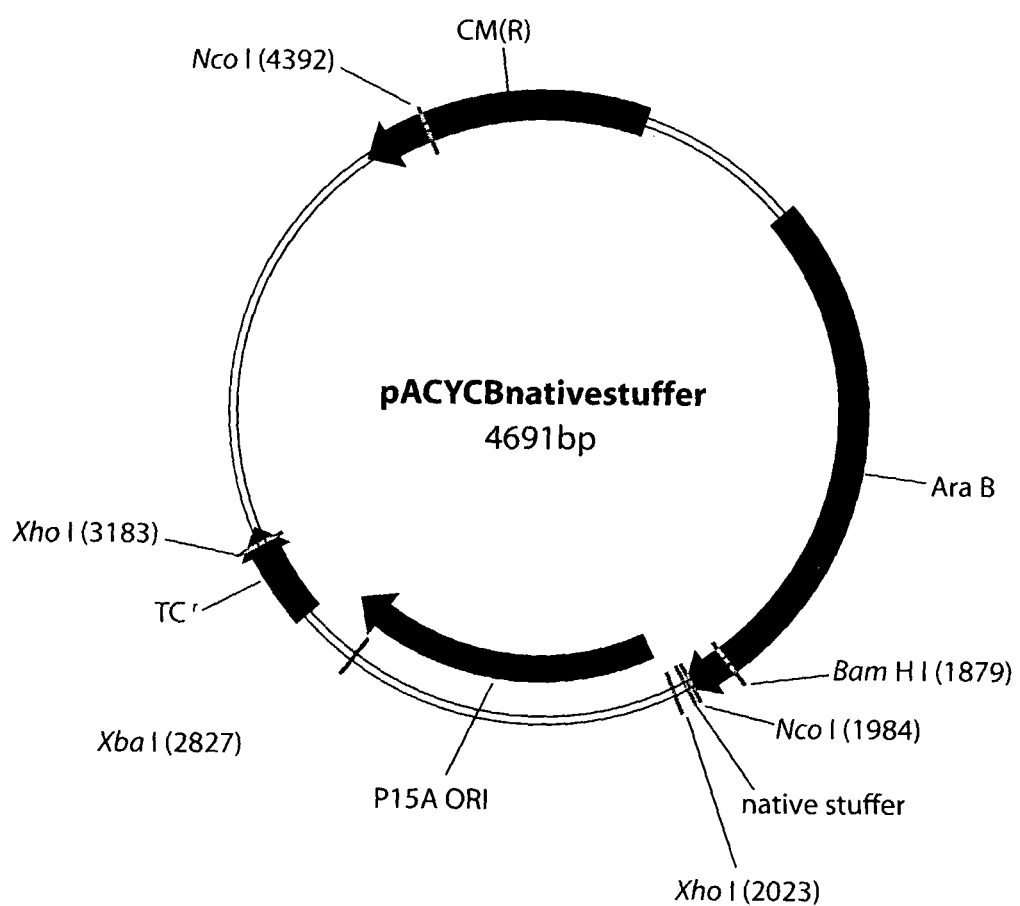

FIG. 14. shows the pACYCB native stuffer vector.

Figure 15:
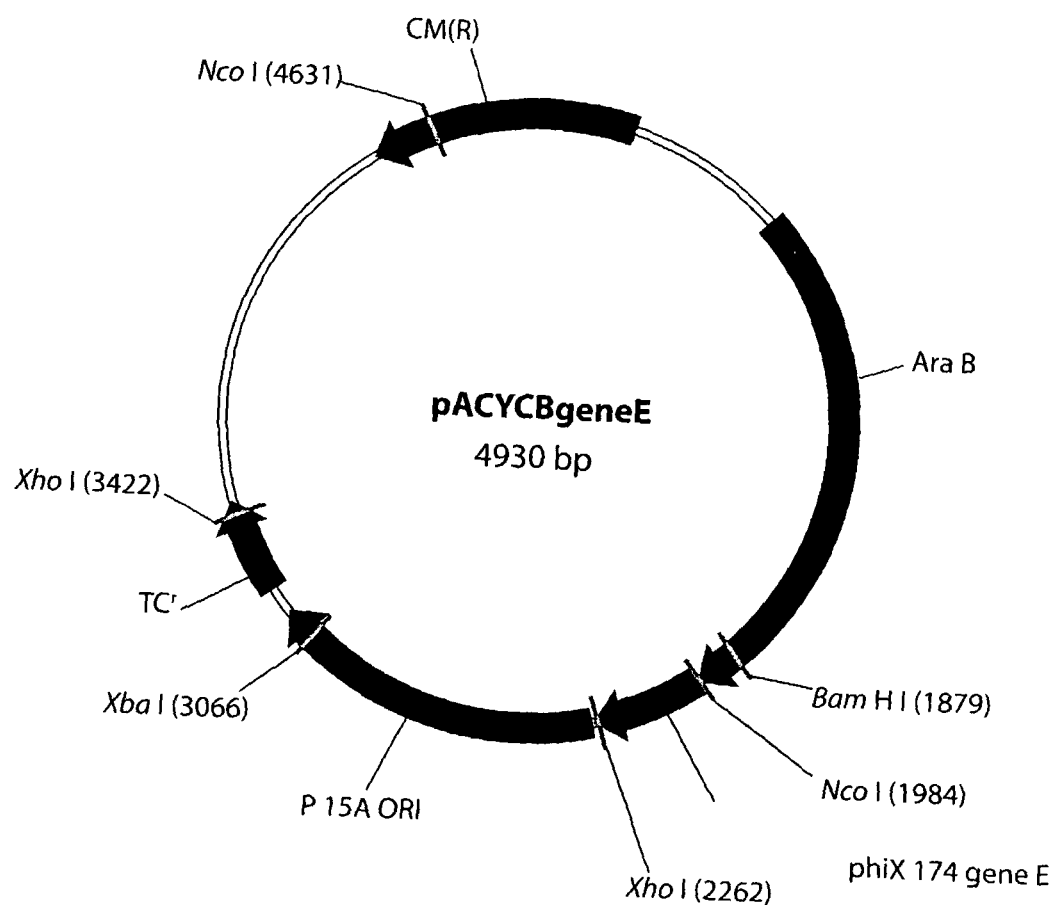

FIG. 15. illustrates the pACYCB gene E vector.

Figure 16:
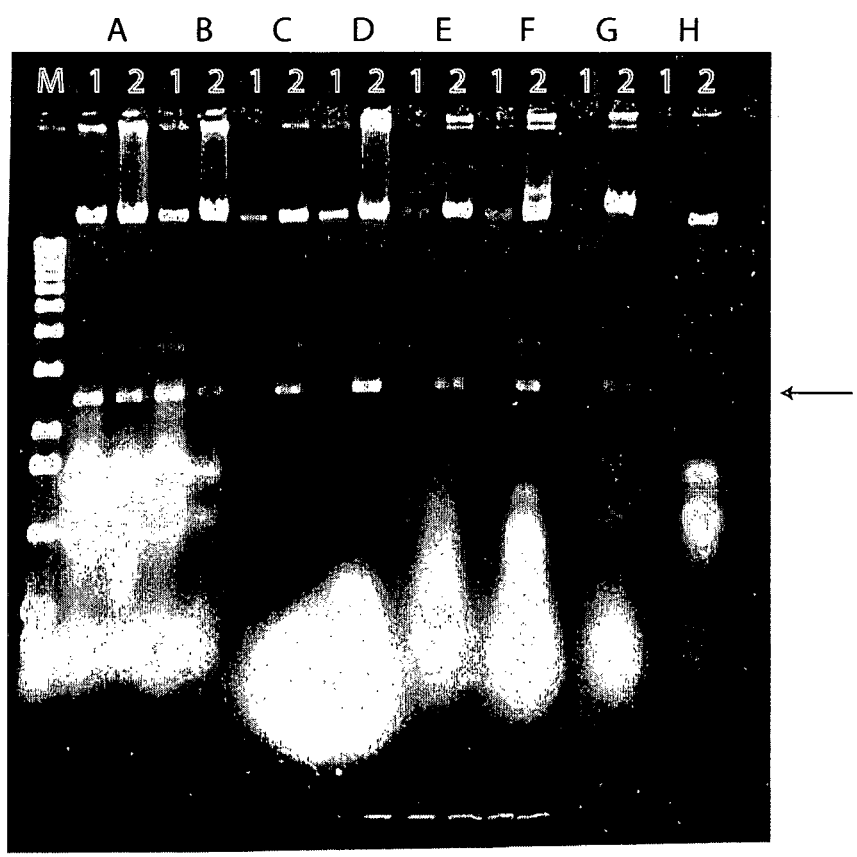

FIG. 16. shows gene E lysis protein mediated plasmid release.

Figure 17:
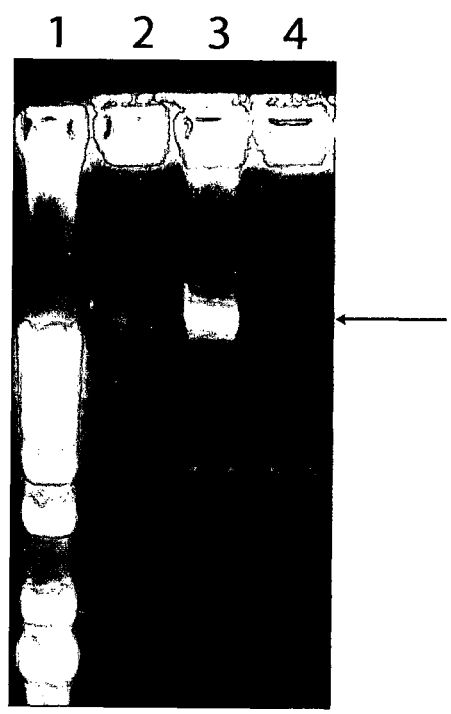

FIG. 17. illustrates nuclease elimination of genomic DNA after antibiotic induced autolysis.

Figure 18:
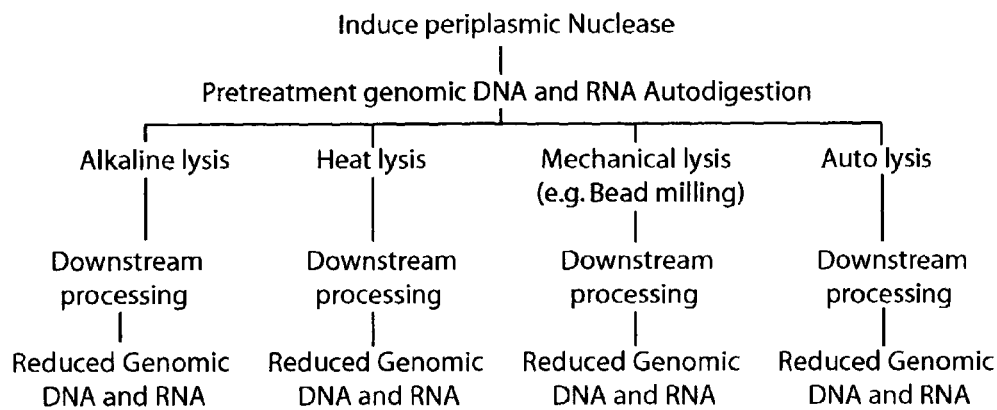
Figure 18:
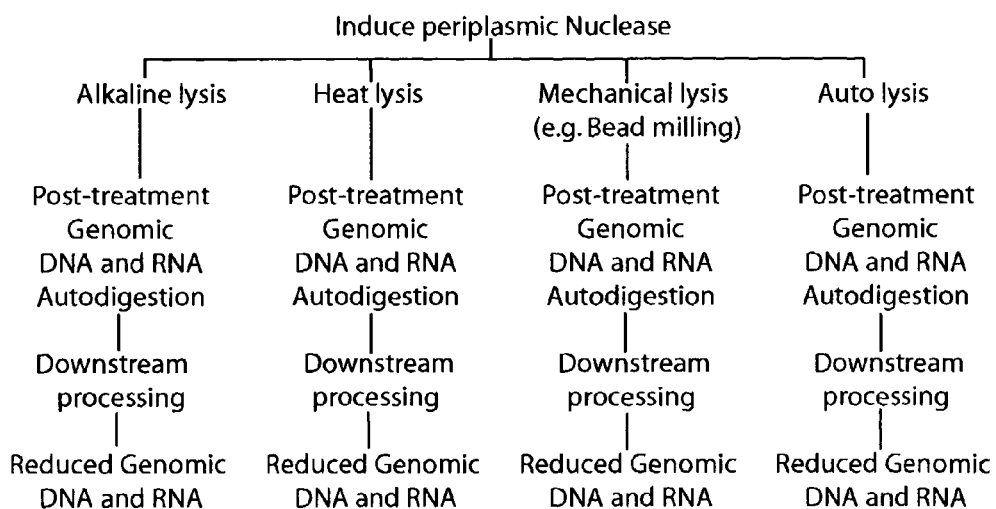

FIG. 18. illustrations the use of periplasmic nuclease-expressing production hosts in plasmid manufacture.

Figure 19:
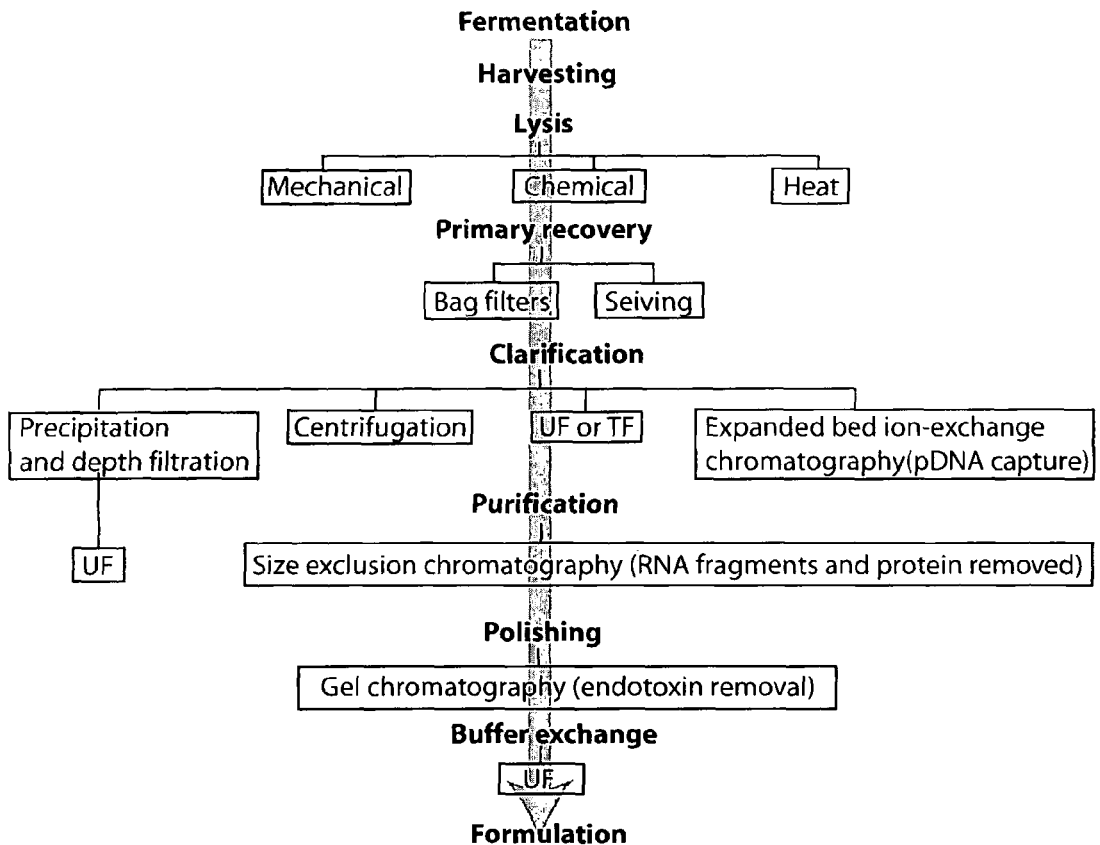
Figure 19:
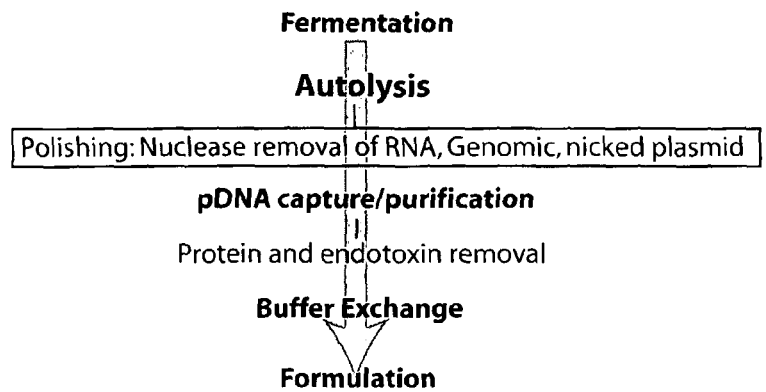

FIG. 19. Illustrates the use of periplasmic nuclease-expressing production hosts in an autolytic plasmid production process.

DETAILED DESCRIPTION OF THE INVENTION

Turning now to the drawings, FIG. 1. shows digestion of denatured plasmid and *E. coli* genomic DNA by T5 exonuclease in a large scale plasmid preparation: 1) DNA molecular weight marker [the largest band is 12 kilobases]; 2) In process plasmid sample from large scale plasmid preparation; 3) Same sample, control T5 exonuclease reaction without T5 exonuclease addition; 4) Same sample, digested with 2% w/w T5 exonuclease. The bottom band is super-coiled, the middle band is a mix of super-coiled dimer and nicked monomer, the top band is a mix of nicked dimer and genomic DNA. Genomic DNA and nicked plasmid are quantitatively removed from the middle and top band. Similar results are seen with 1% w/w T5 exonuclease.

In FIG. 2., the pVEXSapIStuffer vector is illustrated.

In FIG. 3., a method for directional amplification and cloning of cDNA sequences into pVEX vectors is illustrated: A) Plasmid containing two unique address tags, created by digestion with class IIS enzymes located between cuts; and B) Typical primer, containing a class IIS enzyme recognition signal (SapI), at least one intervening nucleotide, and an overlapping region with a unique, non-palindromic sequence (GGG, the address tag in this example).

In FIG. 4. the pVEXSapIOmpAStuffer vector is illustrated.

In FIG. 5. the pVEXBSapIOmpAStuffer vector is shown.

In FIG. 6. the pVEXBOmpARNase vector is illustrated.

In FIG. 7. the pVEXBOmpAT5RNase vector is shown.

In FIG. 8. the T5RNase exonuclease removal of genomic DNA is shown. A gel photo of plasmid DNA preparations with and without the preferred T5 exonuclease and RNase gene(s) is illustrated: Lanes 1, 5, and 9 are T5RNase induced; Lanes 3, 7, and 11 are T5RNase uninduced; Lanes 2, 6, and are RNase induced; and lanes 4, 8 and 12 are RNase uninduced. Samples 1-8 are Qiagen-prepared post alkaline lysis nucleic acids. Samples 9-12 are rapid-extracted total DNA. Samples 5-12 are from 4° C. stored cells, while samples 1-4 are from −20° C. stored cells. The M) marks the DNA molecular weight marker. The largest band is 12 kilobases. From the top, the highest molecular weight band is genomic DNA (gDNA), while next band is super-coiled dimer plasmid DNA [pDNA(2×)], the next band is super-coiled monomer plasmid DNA (pDNA) and the fastest migrating band is RNA (RNA). The arrow in lane 1 highlights reduction of genomic DNA.

In FIG. 9. an illustration of use of S-peptide and S-protein association to make RNaseS-T5 chimera is shown.

In FIG. 10. the nucleic acid hydrolysis by a chimeric nuclease is shown.

In FIG. 11. the RNA reduction with Speptide-T5+Sprotein and T5RNase constructs is shown. Alkaline lysates were prepared from induced cultures of DH5α cells containing the indicated plasmids, nucleic acids were precipitated with ethanol and resolved on 1% agarose gel. RNA (main band) was detected by post-staining with SYBR Green II (Molecular Probes): Lane 1=pVEXBOmpAS-peptideT5+pACYCBOmpASProtein; Lane 2=pVEXBOmpAT5-Speptide+pACYCBOmpASProtein; Lane 3=pVEXBPhoARNase; Lane 4=pVEXBOmpAT5RNase; Lane 5=pVEXBOmpAT5; and Lane 6=pVEXBPhoA(frameshift)RNase(negative control).

In FIG. 12., RNA and genomic DNA reduction with Speptide-T5+Sprotein construct is shown. Alkaline lysates were prepared from induced (lanes 1-4 and 6) and uninduced (lane 5) cultures of DH5α cells containing the indicated plasmids, nucleic acids precipitated with ethanol and resolved on 1% agarose gel. RNA and DNA were detected by post-staining with SYBR Green II: Lane 1=pVEXBOmpAS-peptideT5; Lane 2=pVEXBOmpAS-peptideT5+pACYCBOmpASProtein; Lane 3=pACYCBOmpASProtein; Lane 4=pVEXB-PhoASpeptide-T5; Lane 5=pVEXBPhoASpeptide-T5+pA-CYCBOmpASprotein (uninduced); and Lane 6=pVEXBPhoASpeptide-T5+pACYCBOmpASprotein (induced). Arrows highlight reduction in RNA band (bottom) and genomic DNA band (top) in lane 2.

In FIG. 13. the release of *E. coli* cytoplasmic contents through PhiX174 gene E pore is shown.

In FIG. 14. the pACYCB native stuffer vector is shown.

In FIG. 15. the pACYCB gene E vector is illustrated.

In FIG. 16. the gene E lysis protein mediated plasmid release is shown. Cells cultured with pACYCB gene E+pD-NAVACCUltra-EGFP from 1 are uninduced, 2 are induced 40 min with arabinose: A=Total nucleic acids (pellet); B=Total nucleic acids (pellet) remaining after PI buffer extraction; C=PI (50 mM Tris, 10 mM EDTA, pH 8) extracted nucleic acids; D=LB (media) nucleic acids; E=PBS extracted nucleic acids; F=10 mM Tris pH 8.5 extracted nucleic acids; G=50 mM sodium phosphate, 0.3 M NaCl pH 7 extracted nucleic acids; and H=10 mM MgCl$_2$ extracted nucleic acids. The M) marks the DNA molecular weight marker. The largest band is 12 kilobases. From the top, the highest molecular weight band is genomic DNA (gDNA), while next band is super-coiled dimer plasmid DNA [pDNA(2×)] and nicked monomer plasmid, the next band is super-coiled monomer plasmid DNA (pDNA; arrow) and the fastest migrating bands are RNA (RNA).

In FIG. 17. nuclease elimination of genomic DNA after antibiotic induced autolysis is shown: Lane 1=DNA molecular weight marker; Lane 2=Total DNA after autolysis (pACYCBT5RNase+gWizGFP strain); Lane 3=Total DNA after autolysis (pACYCBNative stuffer+gWizGFP strain); and Lane 4=Sample from lane 2, after incubation 30 min 37° C. The arrow highlights the eliminated genomic DNA band in the T5RNase strain.

In FIG. 18. the use of periplasmic nuclease-expressing production hosts in plasmid manufacture is shown. Format 1 utilizes a pretreatment prior to cell lysis to remove genomic DNA, nicked or linear plasmid, and/or RNA, while format 2 utilizes a post-treatment (or concurrent treatment) after cell lysis to remove genomic DNA, nicked or linear plasmid, and/or RNA.

In FIG. 19. the use of periplasmic nuclease-expressing production hosts is illustrated in an autolytic plasmid production process.

DEFINITIONS autolysis: Lysis methods that cause the cell to undergo self lysis, such as β lactam induced cell lysis, phiX174 phage lysis protein induced ghosting, T4 or lambda phage induced cell lysis by phage lysozyme/phage holin coexpression etc.

ccc: Covalently Closed Circular chimeric enzyme: Fusion between an enzyme and a second protein, for example a fusion of phage T5 D15 exonuclease and fragments or entirety of bovine RNase A DNA replicon: plasmids, cosmids, bacterial artificial chromosomes (BACs), bacteriophages, viral vectors and hybrids thereof ghost band: Denatured ccc DNA DNA: Plasmid DNA phage lysis proteins: Proteins cause the cell to undergo self lysis or ghosting such as ghosting induced by phiX174 phage lysis protein, or cell lysis induced by T4 or lambda phage lysozyme-holin coexpression plasmid: plasmids, cosmids, bacterial artificial chromosomes (BACs), bacteriophages, viral vectors and hybrids thereof plasmid-safe nuclease: Exonuclease that degrades various forms of DNA but not covalently closed circular (ccc) DNA including plasmid DNA RNase: Ribonuclease RNaseA: Bovine pancreatic ribonuclease A T5 exonuclease: Bacteriophage T5 D15 exonuclease The invention relates to methods for reducing genomic DNA during the purification of plasmid DNA (pDNA) using the gram negative bacterium *E. coli* as a production host, using a mechanical fermentation vessel.

A major problem of purification technology has been the separation of pDNA from *E. coli* genomic DNA. The invention is a method for reducing genomic DNA during isolation of covalently closed circular (ccc) DNA. A cost effective approach has been developed that utilizes nucleases in plasmid manufacture. A 'plasmid-safe' nuclease is secreted to the periplasmic space, thus protecting the cell during cell growth, and contact between the nuclease and genomic DNA is controlled to occur at harvest, or during cell lysis.

Nuclease Production Preferred Embodiments

In one preferred embodiment of the invention (FIG. 10), one or more specialized 'plasmid-safe' hydrolytic enzymes (such as the T5 D15 exonuclease, RecBCD exonuclease, other ATP-dependent exonucleases, Exonuclease III, Exonuclease VII, or chimeric, hybrid enzymes), are secreted into the periplasmic space by means of a signal peptide or its equivalent, whereupon the enzyme(s) remain sequestered until cell growth and pDNA induction/production is complete. Upon controlled re-joining of the enzyme with the cytoplasmic contents (through membrane rupture or controlled re-entry into the cytoplasm), the enzyme digests or hydrolyzes unwanted bacterial materials, such as nucleic acids (DNA, RNA), proteins, carbohydrates, lipopolysaccharides, etc.), resulting in a substantially purified plasmid DNA.

Native nucleases may be utilized. Any plasmid-safe nuclease can be utilized such as RecBC (Exonuclease V), and RecBCD exonucleases, related gram positive RexAB or AddAB exonucleases, Archeon exonucleases (e.g. *Geobacillus kaustophilus* AddAB) other ATP-dependent exonucleases, Exonuclease III, Exonuclease VII. This is not an exhaustive list and nucleases from *E. coli*, or from other bacterial, archeon, or eukaryotic source are contemplated. Nucleases such as bacteriophage T5 D15 exonuclease that remove 'ghost bands' are preferred.

In the case of plasmid-safe thermophilic nucleases, it may not be necessary to secrete the nuclease to the periplasm, if the activity of the enzyme is sufficiently reduced at the required growth temperature. This would allow additional genomic reduction methodologies to be utilized, such as heat treatment (42-95° C.) during fermentation.

The invention contemplates use of 'plasmid-safe' exonucleases that digest genomic and preferably denatured and nicked plasmid DNA, without digesting super-coiled plasmid DNA. Preferably, bacteriophage T5 D15 exonuclease (T5 exonuclease) is a candidate DNase to use in plasmid processing. T5 exonuclease does not digest super-coiled plasmid, but is able to digest not only linear single- and double-stranded DNA (Sayers J R, and Eckstein F. 1990 *J. Biol. Chem.* 265:

18311-18317), but also DNA with denaturation loops, such as 'ghost or shadow band' DNA, which often retains biological activity and is retractile to restriction enzyme digestion (Sayers J R, Evans D, and Thomson J B. 1996 *Anal. Biochem.* 241: 186-189). We have demonstrated that purified T5 exonuclease can be utilized to specifically eliminate all non supercoiled DNA species present in samples from a large scale (1 gm) plasmid preparation (FIG. 1).

Chimeric nucleases are also contemplated. This could potentially be done by associating the nuclease enzyme with a fusion partner that is itself resistant to inactivation or removal during alkaline lysis or other contemplated large scale plasmid preparation methodologies. The fusion partner may be any protein or peptide that confers the desired stabilization or localization property. In a preferred embodiment, a chimeric nuclease, in which T5 D15 exonuclease, a 'plasmid-safe' nuclease, is fused to a fusion partner, is utilized. For example, bovine pancreatic RNase A is resistant to inactivation or removal during the harsh alkaline lysis plasmid preparation procedure. As well, RNase A expressed in *E. coli* is recovered in active form in cleared supernatants from alkaline lysis. Alternatively, fusion to thioredoxin (Lu Z, DiBlaio-Smith E A, Grant K L, Warne N W, LaVallie E R, Collins-Racie L A, Follettie M T, Williamson M J, and McCoy J M 1996 *J Biol. Chem.* 271:5059-5065), the C-terminal-solubilizing domain of alpha-synuclein (Kim J S. 2003, US Patent Application 2003/0125522; Park S M, Ahn K J, Jung H Y, Park J H, and Kim J. 2004 *Protein Eng. Des. Sel.* 17:251-60), the thermostable Ftr from *Methanopyrus kandleri* (de Marco A, Casatta E, Savaresi S, Geerlof A. 2004 *J. Biotechnol.* 107:125-33) or to other proteins that increase the stability of fusion partners (Zhou P, Alexey L, and Wagner G. 2003 US Patent Application 2003/0092885; Sanders M C. 2002. US Patent Application 2002/0142384), are also contemplated.

Most preferably, it would be desirable to combine RNase and DNase enzyme activities in a manner that would be compatible with DNA processing procedures. One way to do this would be to develop strains of bacteria in which hybrid enzymes, containing at least RNase and DNase activities, are coexpressed. In order for this approach to be successful, it would be necessary to secrete them initially into the periplasm (to protect the cell from nucleolysis), and to protect the DNase enzyme from losing its activity during lysis.

We demonstrate herein removal of genomic DNA and RNA during plasmid production in several cell lines expressing periplasmically localized T5 exonuclease fused with RNaseA or RNaseS. We have demonstrated that these fusion enzymes have application in removal of contaminant nucleic acids during plasmid processing by alkaline lysis, autolysis or extraction.

The use of T5 exonuclease in a production host to improve plasmid DNA production is not suggested or implied in the prior art. The combination of RNase and DNase nucleases into a chimeric nuclease is also not suggested in the prior art. Additionally, the use of chimeric nucleases in plasmid production are not suggested in the prior art. The novel fusions of T5 exonuclease and RNase reported herein allows simultaneous reduction of two key nucleic acid contaminants. In addition to combining two important elements, the RNase element unexpectedly improved the activity of the DNase moiety (FIG. 12). This synergistic result improves the performance of the chimeric nuclease versus the unfused parental constructs. As well, a single protein entity is easier to engineer into production cell lines, and control during expression, than two components (e.g. RNase and T5 exonuclease) that do not associate.

Plasmid Production Process Preferred Embodiments

Cells expressing a plasmid-safe nuclease are produced in fermentation culture. After production, plasmid is purified from the cells. Plasmid purification can preferably utilize alkaline lysis, heat lysis or mechanical lysis methods described in the art.

Genomic DNA reduction may occur before and/or during and/or after lysis. Genomic reduction may also occur during plasmid extraction, as under osmotic shock (Baker, M, Taylor M, and Uppal S. 2003 WO 03/046177A1) wherein the periplasmic or secreted nuclease of the invention eliminates genomic DNA during DNA extraction from the cell.

Plasmid safe nuclease containing strains are utilized in two preferred plasmid purification formats (formats 1 and 2, FIG. 18).

Format 1 involves elimination of genomic DNA (and RNA with chimeric nucleases) prior to cell lysis (pretreatment step). The nuclease is introduction into the cytoplasm post production (i.e. inner membrane permeabilization). We have demonstrated RNA and genomic DNA reduction in alkaline lysis with pretreatment (format 1) using OmpAS-peptideT5+ OmpASProtein constructs (FIG. 11-12) and OmpAT5RNase (FIG. 8) constructs.

Inducible membrane disrupting factors such as bacteriophage holins or membrane disrupting chemicals or detergents potentially can be used in tandem to selectively introduce the hydrolytic enzymes directly into the cytoplasm at the end of the fermentation cycle, before processing begins. This pretreatment would allow some control over the extent of digestion within the cell before processing the cell paste. This improvement would eliminate the need for protecting the enzymes from lysis reagents (as they would be active before lysis). As well, in this format endogenous nucleases such as RecBCD can participate in targeted genomic DNA degradation.

Format 2 involves elimination of genomic DNA (and RNA with chimeric nucleases) without addition of a defined pretreatment step. Genomic DNA reduction can occur during cell preparation or during or after lysis. If reduction occurs after lysis, stabilization of the enzyme through cell lysis conditions, and subsequent post treatment to activate the enzyme might be necessary. In the case of heat lysis and alkaline lysis, this could require increased thermostability or alkaline SDS stability respectively, and subsequent buffer exchange to remove high concentration of EDTA and SDS. We have demonstrated RNA and genomic DNA reduction in autolysis without pretreatment (format 2) using the OmpAT5RNase (FIG. 17) construct.

Format 2 also has promise for alternative lysis methods such as mechanical lysis in presence of compactation agents (Wilson R C and Murphy J C. 2002 US Patent Application 20020197637), or mechanical lysis with microfluidization (impinging-jet homogenizer) or bead milling (Jem K J 2002 U.S. Pat. No. 6,455,287) that do not require thermostability, or alkaline SDS stability.

In a preferred embodiment, cells are lysed utilizing autolysis. One method of autolysis is to disrupt cells by addition of cell wall disrupting agents, such as B lactam antibiotics to the fermentation. Alternatively lysozyme, or phage encoded peptide antibiotics, can be produced by the host strain to disrupt the cell. Recombinant lysozyme can be expressed by the cell in cytoplasmic form, and released to the periplasm at the desired time by coexpression of a holin (membrane spanning peptide or protein) that creates a channel allowing leakage of lysozyme, and other cytoplasmic proteins, from the cytoplasm to the periplasm. Example lysozyme/holin combinations that can be utilized are known in the art and included herein by reference.

Autolysis conditions, as opposed to alkaline or heat lysis, do not selectively denature genomic DNA. The product of lysis is very viscous, creating processing problems.

We demonstrate herein the novel observation that autolysis, such as antibiotic or phage mediated lysis, in the presence of a plasmid-safe nuclease results in selective removal of genomic DNA and reductions in viscosity (FIG. 17).

This combination of autolysis with a plasmid-safe nuclease is not suggested or implied in the art. Indeed, autolysis methods have not been contemplated for use in plasmid production perhaps due to the high levels of genomic DNA contamination present without the plasmid-safe nucleases of the invention. Autolysis methods to date have been contemplated for use only in production of non-DNA bio-molecules and often incorporate non specific nuclease to eliminate plasmid and genomic DNA. The plasmid-safe nucleases of the invention facilitate the new use for a variety of autolysis methods for large scale manufacture of plasmid DNA.

Autolytic plasmid purification also solves a problem previously thought insolvable, namely, elimination of multiple cell lysis and clarification steps in plasmid processing. A typical plasmid purification process can be dramatically shortened and made cost effective by incorporation of the autolytic purification of the invention (FIG. 19). This eliminates toxic reagents and multiple elements (steps) of plasmid purification without loss of capability.

Nuclease Production

Expression of the nuclease gene may be driven by constitutive or, more preferably, inducible promoters. Inducible promoters that are preferred include, but are not limited to, lambda P R and P L, other phage promoters such as T5, T7, synthetic promoters such as tac and trc, endogenous promoters such as lac, cold shock promoters (cspA), araBAD, stationary phase or starvation promoters, growth rate (rmf) pH (cadA) or anoxia responsive (nar) promoters. Induction can be by increased temperature (PL, tac), decreasing temperature (cspA; cold shock promoter) with thermostable repressors (lambda repressor, lac repressor), inducers (IPTG for tac, trc and lac; Arabinose for AraBAD) or other means (e.g. entry into stationary phase, pH or oxygen shift, glucose or amino acid starvation; reviewed in: Makrides S C. 1996 *Microbiol. Rev.* 60:512-538). Alternatively, the gene may be induced by a regulated antisense RNA.

Several periplasmic or extracellular targeting signal peptides are known in the art and are included herein by reference (e.g. Choi J H, and Lee S Y. 2004 S *Appl. Microbiol. Biotechnol.* 64: 625-635). Exemplary leader peptides for targeting the periplasm are OmpA, PhoAOmpT and PelB.

The nuclease may also be membrane anchored utilizing known anchoring tags such as "anchored periplasmic expression" using leaders such as the NlpA leader and first six amino acids (Harvey B R, Georgiou G, Hayhurst A, Jeong K J, Iverson B L, and Rogers G K. 2004 Proc. Natl. Acad. Sci. 101: 9193-9198). Alternatively, the nuclease may be secreted from the cell into the growth media, and contact genomic DNA during lysis.

Alternatively, nucleases may be engineered to enhance activity or stability, or partitioning during purification (Collen A, Ward M, Tjemeld F, and Stalbrand H. 2001 *J. Chromatogr. A.* 910:275-84), using site directed mutagenesis, addition of small peptide targeting tags, or directed evolution (Zhao H, Chockalingam K, and Chen Z. 2002 *Curr. Opin. Biotechnol.* 13:104-10) using molecular breeding approaches (Ness J E, Kim S, Gottman A, Pak R, Krebber A, Borchert T V, Govindarajan S, Mundorff E C, and Minshull J. 2002 *Nat. Biotechnol.* 20:1251-5; Kurtzman A L, Govindarajan S, Vahle K, Jones J T, Heinrichs V, Patten P A. 2001 *Curr. Opin. Biotechnol.* 12:361-70).

Porin Systems for Cell Autolysis

There are two classes of phage porin proteins that produce membrane pores. These are known in the literature, and a nonlimiting list of potential porins for practice of the invention is included herein by reference (Young 1992, Supra; Wang I N, Smith D L and Young R. 2000 *Annu. Rev. Microbiol.* 54: 799-825). One class is from double stranded DNA bacteriophages such as T4 and lambda phage of *E. coli*, or bacteriophage LL-H of *Lactobacillus*. These porin proteins are called holins and they assemble in the cytoplasmic membrane, to create pores for cell wall digesting proteins to be released into the periplasm. These holes range from small (T4 t protein that just seems to fit the lysozyme that it leaks from the cytoplasm to periplasm) to big enough that >100 kd proteins such as B galactosidase can fit through (lambda S; inner pore diameter of >10-12 nm, similar in size to steptinomycin O/listerialysin O cytotoxins). We contemplate usage of production strains utilizing these porins and lysozyme in combination with plasmid-safe nucleases of the invention for plasmid manufacture. Autolysis strains utilizing these porins have been created for protein production (Leung and Swartz, Supra, 2001), but utilization in plasmid production has not been described in the art.

Alternatively, single stranded DNA phage, such as PhiX174, produce a single lysis protein (gene E) required for phage release. This protein, and lysis proteins from other single stranded DNA phage, may inhibit cell wall formation in a manner similar to penicillin (reviewed in: Bernhardt T G, Wang I N, Struck D K and Young R. 2002 *Res. Microbiol.* 153: 493-501), The gene E product forms an uM diameter channel between the outer and inner membranes, effectively sealing the periplasm and non-lyrically dumping the cytoplasmic contents including plasmid DNA (Witte A and Lubitz W. 1989 *Eur. J. Biochem.* 180: 393-398), into the media (FIG. 13; reviewed in: Young R, Wang I N and Roof W D. 2000 *Trends Micro.* 8: 120-128). The phiX 174 gene E system is used to make bacterial ghosts, for antigen or DNA vaccine delivery (Jalava K, Iko F O, Riedmann E and Lubitz W. 2003 *Expert Rev. Vaccines* 2: 45-51). For DNA vaccine delivery, the ghosts are backfilled with plasmid DNA. Methods to manufacture ghost have been developed based on the observation that growth in high magnesium (e.g. 0.1 M $MgSO_4$) prevents lysis. Manufacture involves: 1) expression of gene E in the presence of mg; 2) buffer exchange of the cells; and 3) drop magnesium to form channels and dump cytoplasmic content (reviewed in Jalava et al., Supra, 2003).

Bacterial ghosts have not been evaluated for applications in plasmid DNA manufacture and the integrity of released plasmid has not previously been assessed (Witte and Lubitz, Supra, 1989).

Host Strains for Nuclease and or Autolytic Gene Expression

The nuclease gene can be in a plasmid that is compatible with the target plasmid, or most preferably integrated into the genome. Strain engineering can be performed in any strain of bacteria that is suitable for plasmid production.

Strains of bacteria bearing integrated copies of nuclease expression plasmids are made using a variety of techniques, for example lambda red gam recombination (Murphy K C 1998 *J. Bact.* 180: 2063-2071; Datsenko K A, Wanner B L. 2000 *Proc. Natl. Acad. Sci.* (USA); 97:6640-6645). This technique has been utilized successfully in recA-strains such as DH5α, a common plasmid production host. Briefly, the expression cassette (s) including a flanking antibiotic resistance gene is PCR amplified using primers containing sequences homologous to the integration site. The target DH5α strain is transformed with the ampicillin resistant lambda Red recombination function containing plasmid pKD46 and Red recombinase production induced with arabinose. The cells are prepared and electroporated with the PCR fragment as described. Homologous recombinants are selected with kanamycin and cured of the pKD46 helper plasmid by shifting to the non-permissive temperature (pKD46 has a temperature sensitive origin of replication) and loss of ampicillin resistance verified.

Plasmid Production

Strains of E. coli with integrated nuclease genes can be utilized to manufacture plasmid DNA in fermentation culture. Exemplary fermentation processes are known in the art (see Carnes 2005 for a review: Carnes A E. 2005 *BioProcess International*, October 2005, in press). Nature Technology Corporation uses batch and fed-batch processes in animal product free batch (NTC3018) and fed batch (NTC3019) fermentation media optimized for plasmid production. These media were developed to support reduced growth rates and maintain plasmid stability and integrity. Plasmid yields of 1100 mg/L and OD600 of 120 have been achieved with an automated fed-batch fermentation process with feeding controlled to maintain a specific growth rate of 0.12/h.

We contemplate utilizing host strains elaborating plasmid-safe nucleases to produce plasmid enriched feed streams from fermentation culture in exemplary plasmid purification processes. The combination of nuclease strains with high yield fermentation and exemplary purification process may provide cost effective methodologies to further reduce genomic DNA levels to acceptable levels for gene therapy and DNA vaccination applications.

EXAMPLES

The method of the invention is further illustrated in the following examples. These are provided by way of illustration and are not intended in any way to limit the scope of the invention.

Example 1 pVEX Expression Vectors

The pVEXSapIstuffer protein expression vector is shown in FIG. 2. The plasmid has a pBR322 origin of replication (ROP deletion) and ampicillin resistance marker.

This vector has an inducible Tac promoter driving expression of the gene of interest in *E. coli*. Expression is repressed by the lacIq gene product (encoded on the plasmid) and induced by addition of IPTG to the culture.

Genes of interest are cloned into a 'stuffer' that consists of SapI type IIS cloning sites that generate ATG and TAA sticky ends as outlined in FIG. 3. Genes are copied by amplification from clones or genomic DNA using primers with generic address tags, and unique-sequence specific sequences. Internal SapI sites in the target gene are generally not detrimental since there is only a 1/16 chance that an internal SapI site would match one of the address tags.

A derivative of this plasmid, pVEXSapIHNtagstuffer fuses the gene of interest with an N terminal HN tag which is followed by an enterokinase cleavage site. This tag binds immobilized metal affinity chromatography (IMAC) resin similarly to the histag, affording affinity purification. Genes are PCR amplified with primers incorporating SapI sites into termini to generate 5' AAG (last lysine residue of enterokinase cleavage site) and 3' TAA 3 bp sticky ends upon digestion with SapI (New England Biolabs, Beverley N J).

Example 2

Construction of pVEXSapIOmpA Secretion Vector

The OmpA secretion signal peptide was engineered into the pVEXstuffer vector as follows. Oligonucleotides encoding the OmpA secretion signal peptide were annealed and cloned into the NcoI site of pVEXSapI stuffer to make pVEXSapIOmpA stuffer. The resultant clone expresses the OmpA leader that targets the protein of interest to the periplasm. The OmpA leader is cleaved off, leaving the protein of interest with a 2 amino acid leader (Ala-Thr) prior to the Met codon of the gene of interest. A map of this vector is shown in FIG. 4. Cytoplasmic constructs can be converted to secreted constructs by transfer of the NcoI/XhoI fragment containing the gene of interest into this vector. The OmpAHNtagstuffer, encoding an N terminal HN tag, was constructed exactly as described above using NcoI digested pVEXSapIHNtagstuffer for annealed oligo insertion.

Example 3

Construction of pVEXOmpAHNRNase Expression Vector

The bovine pancreatic RNase gene was PCR amplified from bovine genomic DNA All PCR was performed using Pfu DNA polymerase (to avoid adding extra bases onto the ends of blunt fragments) using standard PCR methodologies.

The 400 bp PCR product was digested with SapI, and the 100 and 300 bp fragments (internal SapI site) gel purified and cloned into SapI digested pVEXOmpAHNstuffer vector using standard cloning methodologies. Recombinants (pVEXOmpAHNRNase) were sequence verified.

Example 4

Cloning T5 Exonuclease

The T5 D15 exonuclease gene was PCR amplified from phage T5 (ATCC 11303-B5), cloned, and the sequence confirmed. The 900 bp fragment was purified and used as a template to PCR an HNstuffer compatible fragment. These fragments were purified and blunt end cloned into the SmaI site of pW2.0 vector, a pUC19 derivative with a modified polylinker. pW2.0-T5 and pW2.0-HNT5 clones were isolated and sequence verified.

Example 5

Construction of pVEXBOmpAstuffer Expression Vector

A second expression system, with lower leaky expression and lower overall inducible expression, was constructed. This vector, pVEXBSapIOmpAstuffer contains the AraBAD promoter and is inducible by arabinose addition, as opposed to IPTG induction for the tac promoter containing parent pVEXSapIOmpAstuffer vector.

The Ara BAD promoter and flanking araC repressor was PCR amplified from DH5α genomic DNA. This amplified product (1.3 kb) was digested with AarI and cloned into EcoRI/XhoI digested pVEX vector. The resultant clone contained the AraBAD operon downstream of the stuffer. The AraBAD region was excised with XhoI and EcoRI, and the sticky ends blunted by filling with dNTPs and klenow. The 1.3 kb fragment was cloned into the 2.8 kb backbone fragment of pVEXSapIOmpAstuffer (bp 247-3108) and pVEXSapI-OmpAHfNtagstuffer vectors. The backbone fragments were obtained by gel purification of vector digested with MluI and XbaI, blunted with klenow and dNTP, and CIP treated. Resultant clones were screened for orientation of the Ara-BAD locus by restriction digestion and sequence verified. The final constructs, pVEXBSapIOmpAstuffer (FIG. 5) and pVEXBSapIOmpAHNtagstuffer, replaces the lacIq gene and tac promoter with the Ara C repressor and ara BAD promoter.

Example 6

Construction of pVEXBOmpAHNRNase

The HNRNase gene was excised from pVEXOmpAHNR-Nase by digestion with NcoI/XhoI and transferred into NcoI/XhoI digested pVEXBSapIOmpAHNtagstuffer vector.

Example 7

Construction of pVEXBOmpARNase Expression Vector

The HNtag was deleted from pVEXBOmpAHNRNase by PCR amplification of the entire plasmid using AarI containing primers. PCR amplification resulted in a vector length PCR fragment. Cleavage of purified PCR product with AarI created compatible sticky ends (double underlined in primers) that upon ligation created a precise deletion of the HN tag. Clones of pVEXBOmpARNase (FIG. 6) were isolated and confirmed by restriction digestion and sequencing.

Example 8

Construction of pVEXBOmpAT5RNase Expression Vector

The HNtag was deleted from pVEXBOmpAHNRNase by PCR amplification of the entire plasmid using AarI containing primers. The T5 exonuclease was then cloned into the gapped plasmid. PCR amplification of pVEXBOmpAHNR-Nase resulted in a vector length PCR fragment. PCR amplification of pW2.0T5 with T5-specific primers resulted in a 900 bp T5 gene. Cleavage of purified PCR products with AarI created compatible sticky ends which upon ligation created a precise deletion of the HN tag and insertion of the T5 gene. Clones of pVEXBOmpAT5RNase (FIG. 7) were isolated and confirmed by restriction digestion and sequencing.

Example 9

T5RNase Digestion of Genomic DNA During Plasmid Preparation

DH5α cell lines containing pVEXBOmpARNase (RNase) or pVEXBOmpAT5RNase (T5RNase) plasmids were grown at 37° C. in LB liquid media containing 5 mM $MgSO_4$ and protein expression induced in midlog phase (approximately 0.5 OD600/mL) by addition of arabinose to 0.2%. Cultures were harvested after 4 hrs induction at 29° C. Control uninduced cultures were also grown under identical conditions. Cells were pelleted and stored at −20° C. or 4° C. overnight. Cells from −20° C. storage were thawed and incubated 10 min at 37° C. Cells from 4° C. were processed without additional pretreatment. Lysis was observed in the RNase induced cells, but not in the T5RNase induced, or uninduced cells.

Nucleic acid degradation was assessed in two assays. In the first assay, total DNA was extracted from 4° C. cells utilizing the rapid screening protocol of Williams et. al. (Williams, J. A., Langeland, J. A., Thalley, B., Skeath, J. B., and Carroll, S. B. (1994). Production and purification of polyclonal antibodies against proteins expressed in E. coli. DNA Cloning: Expression Systems, IRL Press). Briefly, cells were resuspended in cell disruption buffer (10 mM Tris pH 8.0, 100 mM NaCl, 10 mM EDTA), extracted with phenol, RNase treated, and DNA resolved on a 1% agarose gel after addition of tracker dye. In the second assay, total nucleic acid (including RNase) was isolated using Qiagen miniprep buffers (P1, P2, N3) and protocol except that the RNase was not added to the P1 buffer (Qiagen QIAprep minprep Handbook, March 2002). After preparing a clarified lysate by centrifugation, the lysate was incubated at 37° C. for 10 min, nucleic acids were precipitated by addition of 3 volumes 95% ethanol, collected by centrifugation, washed with 70% ethanol and resuspended in Qiagen buffer EB (10 mM Tris, pH 8.5) containing 10 mM $MgSO_4$. The sample was incubated 10 min 37° C., tracker dye added, and nucleic acids resolved on a 1% agarose gel.

The results (FIG. 8) demonstrated 'plasmid-safe' specific degradation of genomic DNA by the T5RNase fusion during alkaline lysis plasmid production. The induced cells were viable (continued growth after induction) and did not undergo lysis during freezethaw. Note the complete elimination of chromosomal DNA band (large band >12 kb) in alkaline lysates from induced T5RNase in lanes 1 and 5 compared to uninduced and RNase controls. No degradation of plasmid DNA is observed with −20° C. stored samples (compare lanes 1 and 3; the remaining large band in lane 1 is super-coiled dimer) while complete elimination of genomic DNA, and partial digestion of plasmid DNA is observed with 4° C. prepared samples. This indicates that the different pretreatments (overnight incubation at 4° C. versus freeze thaw and 10 min at 37° C. with −20° C. samples) differentially introduce the nuclease into the cytoplasm. Partial elimination of genomic DNA in total nucleic acid extracts from T5RNase is also observed in lane 9 but is not as complete as the pretreated samples purified by alkaline lysis. The gel was scanned, and the bands from lanes 1-4 integrated and quantified. The results are summarized in Table 1. The genomic DNA level is lower in the RNase induced lane due to the observed cell lysis. Genomic DNA is reduced 50 fold in the T5RNase induced sample, relative to T5RNase uninduced sample, without any reduction in plasmid level. This demonstrates utility of the chimeric nuclease to reduce genomic DNA during plasmid processing.

TABLE 1

| Gel band quantification of lanes 1-4 from FIG. 8 | | | | |
|---|---|---|---|---|
| Band | Lane 1 | Lane 2 | Lane 3 | Lane 4 |
| Supercoiled monomer plasmid | 27103 | 31328 | 21726 | 27180 |
| Supercoiled dimer plasmid | 2160 | 1409 | 3615 | 558 |
| Genomic DNA | 824 | 5967 | 42406 | 23671 |

Example 10

RNaseS-T5 Fusions

Other plasmid-safe chimeric nucleases with T5 exonuclease were created using the S-peptide S-protein system to make chimeric nucleases useful for genomic DNA and RNA removal. Here we describe construction and evaluation of such fusions, and demonstrate utility in plasmid manufacture. These fusions retain both RNase and enhanced DNase activity, as shown below.

It has been demonstrated that fusion of heterologous proteins to the N terminal S-peptide of RNase A acquire RNase activity after association with the S-protein of RNase. The S-peptide is the 20 amino acid N terminal fragment of bovine pancreatic RNase A is released by subtilisin cleavage; the C terminal fragment (21-124) is the S-protein. The S-protein and S-peptide bind with high affinity ($3.1 \times 10^{-11}$ M at pH 8.3) as RNase S, which has similar enzyme activity to native RNase7. The S-tag system (McCormick M and Mierendorf R. 1994 *In Novations* 1: 4-7) is a protein purification system that has been utilized to fuse heterologous proteins to functional RNase. The S-tag is the N terminal 15 amino acid residues of the S-peptide, and, even when fused to a heterologous protein, interacts with S-protein to generate active RNase. The S-tag (and S-peptide) is highly soluble, expressed to high level in *E. coli*, and can mediate high affinity interaction with S-protein when fused at either terminus. Reagents, based on association with S-protein (S-tag Western Blot) or reconstitution of functional RNase S(S-tag Rapid assay), are commercially available from Novagen to rapidly detect and quantify S tag, or S-peptide, fusions. Utilization of this system to make a chimeric nuclease is illustrated in FIG. 9.

pVEXB OmpA-S-protein fuses the OmpA secretion leader sequence (signal sequence) to the S-protein fragment of RNase. Two versions were created, encoding either a fusion of OmpASprotein(16-124) or OmpASProtein(20-124). Both shown similar function in vivo. These constructs are designed to release the precise S-protein fragment after cleavage of the OmpA leader during periplasmic secretion. The expression cassette from these constructs was transferred to pACYC177 (compatible with pVEX) for coexpression studies. pACYC177 is lower copy number than pVEX, so less S-protein than S peptide should be made. This is by design, since S peptide may be required to facilitate the folding of S-protein.

The S-peptide (for association with the S-protein) was fused to either the N terminus of T5 exonuclease (S-peptide-T5) to make a secreted S-peptide-T5 fusion vector (pVEX-BOmpA S-peptide-T5) or the C terminus to make a secreted T5-Speptide vector (pVEXBOmpA T5-Speptide). The OmpA or the PhoA secretion leader sequence were utilized, to precisely release the native N terminus of the S-peptide.

When coexpressed, the Speptide and Sprotein fragments are designed to associated as RNaseS, confiring RNase function, as well as DNase function from the fused T5 exonuclease.

Example 11

Plasmid Purification RNaseS-T5 Fusions

The overall strategy to reduce genomic DNA, using RNaseS-T5 as an example, is shown in FIG. 10. Expression and analysis was performed as described in Example 9 for T5RNase. Reductions in genomic DNA and RNA are observed with cell lines expressing these fusions (FIG. 11-12). The OmpAS peptide-T5 construct, in the presence of either OmpASprotein construct (16-124 or 20-124), reduced genomic DNA and RNA compared to either construct alone. The OmpAT5-Speptide construct was proteolytically sensitive (degradation bands detected by SDS-PAGE analysis) and as expected had reduced RNase and DNase activity compared to the OmpASpeptide-T5 construct. All the other T5 or Speptide-T5 constructs were proteolytically stable (a band of the expected size was observed by SDS-PAGE analysis). This demonstrates enhancement of activity of T5 exonuclease by association with RNase S, which also retains RNase activity.

Example 12

Construction of PhiX174 Gene E Expression Vector

The phiX174 gene E protein was cloned under AraBAD control on a plasmid that is compatible with existing high copy pUC origin plasmids (e.g. gWiz-GFP, pDNAVACCU1-tra-EGFP) and pBR322 origin plasmids (e.g. pVEXBT5RNase).

pVEXB-Native Stuffer pVEXSapIstuffer vector was digested with XbaI and MluI. The sticky ends were filled with Klenow and dNTP and heat killed. The ends were dephosphorylated with calf intestinal phosphatase. The 2.8 kb fragment was gel purified from the 1.5 kb fragment. pVEXB vector was digested with EcoRI and XhoI. The sticky ends were filled with Klenow and dNTP. The 1.3 kb fragment containing the araB promoter was gel purified from the 4.3 kb. The fragments from steps 1 and 2 were ligated, transformed and screened on Amp. The clone (pVEXB-Native stuffer) with the correct orientation was selected by restriction digestion and confirmed by sequencing.

pACYCB-Native (FIG. 14) and OmpA Stuffer Vectors

The cassette from the pVEXBOmpAstuffer and native stuffer expression vectors was transferred into a pACYC vector to allow coexpression with pUC and pBR322 based origin vectors (e.g. pVEX and pDNAVACCUltra vectors). CIP treated, gel purified XmnI digested pACYC-RIL plasmid (fragment A) was prepared. pVEXBOmpAstuffer and pVEX-Bnativestuffer, were digested with EcoRI (filled with Klenow and dNTPs) and the smaller fragments (pVEXBOmpAstuffer is 2703, 1466, Fragment B1; pVEXBnative stuffer slightly smaller, Fragment B2) were purified. Fragments A, B1 (pA-CYCBOmpAstuffer) or A and B2 (pACYCBNative stuffer) were mixed and ligated. The ligations were transformed into DH5α competent cells and selected on chloramphenicol agar plates. Clones, and orientation, were confirmed by restriction digestion pACYCB Gene E (FIG. 15)

The phiX174 gene E protein was PCR amplified using 10 ng phiX174 genomic DNA as template. Used 5×45C anneal, 25×55C anneal, with 1 minute extension time at 72C and 30 second denaturation at 95C. pACYC-Bnative stuffer was digested with SapI and the two fragments (4375, 282, 34) purified. The PCR fragment was also digested with SapI. The 3 fragments were mixed and ligated. The ligations were transformed into DH5α and transformed onto LB+Chloramphenicol+glucose (0.2%) (Glucose is added to reduce leaky expression). The pACYCB phiX174 gene E vector was confirmed by restriction digestion, and sequencing.

Example 13

Release of High Copy pUC Origin Plasmid by Gene E Induced Cell Ghosting

Cells lines were created by transformation of Z competent (Zymos) *E. coli* cells with purified plasmids and grown on agarose plates containing antibiotic and 0.2% glucose (to reduce leaky gene E expression from the arabinose promoter). The cell lines were grown in LB media at 37° C. containing 34 ug/mL chloramphenicol (strains containing the gene E expression plasmid) and/or 50 ug/mL Kanamycin (strains containing the pDNAVACCUltra plasmid) or 100 ug/mL ampicillin (strains containing pVEX plasmids) and induced at midlog (approximately 0.5 OD600/mL). Arabinose induction was by addition of arabinose from a 100× stock to 0.2% final concentration. Media extracts for gel analysis were prepared by either 1) using clarified media or 2) phenol chloroform extraction, ethanol precipitation and resuspension in TE. (20× concentration). Cell pellet extracts for gel analysis were prepared by resuspension of the cell pellet in buffer (10-20× concentration), incubation at defined temperature and duration, followed by phenol chloroform extract. The supernatants were analyzed directly by gel electrophoresis. Total nucleic acids in the cell pellets were extracted using cell disruption buffer as described in Williams et. al., Supra, 1994, using 10-20 fold concentration (compared to the original media volume) of cell disruption buffer, and no RNase added. The extracts were analyzed for nucleic acids by agarose gel electrophoresis, and RNA and DNA visualized by poststaining with 1/10,000 diluted SYBR Green II (Sigma).

Nucleic Acid Release by Gene E Lysis Protein Expression

Three cells lines were made and evaluated: 1) pACYC-B-gene E 2) pACYC-B-gene E+pDNAVACCUltra-GFP and 3) pDNAVACCultra-GFP. pDNAVACCultra is a high copy kanamycin resistant pMB1 origin plasmid, compatible with pACYC plasmids.

Cells were either: A) uninduced; or B) induced with arabinose to 0.2%; or C) induced with arabinose to 0.2% in the presence of 0.2 M $MgSO_4$ (to inhibit ghosting). Cells were induced for 30 minutes and aliquots harvested. The supernatants were analyzed for nucleic acids by agarose gel electrophoresis, and RNA and DNA visualized by poststaining with 1/10,000 diluted SYBR Green II (Sigma). The pellets from 1.5 mL cells was resuspended in 100 uL of TE buffer (10 mM Tris, 1 mM EDTA, pH8.0), incubated at RT for 1 hr, and cells pelleted. The TE cell extracts were analyzed by gel electrophoresis as above.

PhiX174 gene E release of plasmid (pDNAVACCultra-GFP) into LB and extraction supernatant was observed after induction. RNA and genomic DNA were also released. Most of the plasmid within the cells was released from the induced sample (without $MgSO_4$) into the media and the TE extract. If gene E was induced in the presence of 0.2 M $MgSO_4$, plasmid was not released into LB, but was released when Mg concentration was lowered in the TE extraction buffer. These experiments demonstrated that culture ghosting occurs in presence of gene E and a high copy plasmid, and that plasmid release is dependent on gene E induction. No plasmid was released from the pDNAVACCUltra alone cell line, demonstrating that plasmid release is dependent on the phiX174 gene E product. As well, plasmid release into the media can be prevented by inclusion of 0.2 M $MgSO_4$ in the media. This allows the cells to be harvested, and buffer exchanged to remove Magnesium, and allow plasmid release.

A time course of phiX174 gene E induced release of pDNAVACCultra-GFP plasmid was performed. Intact plasmid was released from cells after 30-40 min induction.

Plasmid from phiX174 gene E+pDNAVACCultra-GFP uninduced and induced pellets was extracted with PI, TE, PBS, EB (10 mM Tris, pH 8.5), BB (50 mM $PO_4$, 300 mM NaCl) or 10 mM $MgCl_2$. Plasmid and RNA and genomic DNA was extracted under all these conditions (FIG. 16). With PI or EB, the bulk of the plasmid was extracted, with little plasmid remaining in the cell pellet after extraction (Compare lane B2 and B1, FIG. 16). Release of plasmid in EB demonstrates that EDTA is not required for plasmid release. This is advantageous, since it will allow processing without EDTA induced LPS release during processing.

Some differences in relative extraction of plasmid and genomic DNA, and integrity of RNA were observed. For example, less RNA was extracted with BB, 10 mM $MgCl_2$, and PBS while less genomic DNA and plasmid was extracted with 10 mM $MgCl_2$. These salt and cation effects may be optimized to enhance released plasmid purity.

PhiX174 gene E release of pDNAVACCultra-GFP in the presence of spermine was determined, by comparing plasmid release in uninduced, induced, and induced+10 or 30 mM spermine. Release of plasmid and genomic into LB was inhibited by 30 mM spermine, and partially inhibited by 10 mM. No RNA was detected in total pellet or any elutions with 30 mM spermine. Spermine treated cells were resistant to plasmid extraction with PI, TE or EB, but some plasmid was extracted from 30 mM spermine treated cells with PBS, BB (50 mM $PO_4$, 300 mM NaCl) or 10 mM $MgCl_2$. When induced cells were incubated overnight at RT, release of plasmid into media with all three induction conditions was observed. More RNA was released (or compacted) with spermine, and very little nicking of plasmid after overnight incubation in LB was observed. This demonstrated that the released plasmid is stable when stored in media.

PhiX174 gene E mediated release of plasmid was tested with 30 min incubations of cell pellets at RT, 37° C., 55° C. and 65° C. in buffer PI or 50 mM Tris, 10 mM $MgCl_2$, pH 8.0). Plasmid release and integrity was unaffected at RT, 37° C. or 55° C. temperature, some lysis at 65° C. in PI, with plasmid nicking and increased genomic. Some RNA degradation at 37° C. compared to RT with PI, not Tris/mg, was observed.

Collectively, these results demonstrate that gene E lysis protein induced plasmid release is feasible for high yield release of intact plasmid from cells. Plasmid release can be controlled by altering ionic strength/pH of extraction buffer, with or without spermidine, or other compactors in media. The plasmid is stable when released into the media or extraction buffer. This also demonstrates that cell can be buffer exchanged into variety of buffers to release plasmid under conditions for optimal enzymatic removal of genomic DNA/RNA. However, high levels of genomic DNA and RNA are released utilizing this method.

Example 14

Elimination of Genomic DNA and RNA Released by Gene E Lysis Protein Induced Cell Ghosting Nuclease Reduction of RNA and Genomic DNA Five cells lines were made and evaluated: 1) pACYC-B-gene E; 2) pACYC-B-gene E+pDNAVACCUltra-GFP; 3) pDNAVACCultra-GFP; 4) pACYC-B-gene E+pVEXBT5RNase; and 5) pVEXBT5RNase. pVEXBT5RNase is a moderate copy ampicillin resistant pMB1 origin plasmid, compatible with pACYC plasmids, that contains an arabinose inducible nuclease with activity against RNA, genomic DNA, but not super-coiled plasmid.

Cultures were either uninduced or grown 70 min post induction (0.2% arabinose, to induce both gene E and T5RNase), and nucleic acids in culture supernatants, and osmotic shock of cell pellets, evaluated by gel electrophoresis. Induced cells lines containing the PhiX174 gene E lysis protein and pVEXBT5RNase had much reduced genomic DNA released into media when T5RNase was induced. The same effect was observed with osmotic shocked cell pellets (5 mM $MgSO_4$, data not shown). The release of genomic from uninduced cells is due to leaky expression of the lysis protein, that causes ghosting at high OD600 values utilized for the uninduced control in this experiment. This demonstrates co-expression of T5RNase destroys gene E released genomic DNA, and can be utilized, to improve released plasmid purity and reduce viscosity of the lysate.

Example 15

Manufacture of Plasmid DNA Using PhiX174 Gene E Protein Mediated Autolysis

For plasmid manufacture, expression of the porin genes would need to be integrated into the genome. Expression of the porin gene may be driven by inducible promoters. Inducible promoters that are preferred include, but are not limited to, lambda PR and PL, other phage promoters such as T5, T7, synthetic promoters such as tac and trc, endogenous promoters such as lac, cold shock promoters (cspA), araBAD, stationary phase or starvation promoters, growth rate (rmf) pH (cadA) or anoxia responsive (nar) promoters. Induction can be by increased temperature (PL, tac), decreasing temperature (cspA; cold shock promoter) with thermostable repressors (lambda repressor, lac repressor), inducers (IPTG for tac, trc and lac; Arabinose for AraBAD) or other means (e.g. entry into stationary phase, pH or oxygen shift, glucose or amino acid starvation; reviewed in Makrides S C. 1996). Alternatively, the gene may be induced by a regulated antisense RNA. Various inducible phiX 174 gene E expression systems have been developed, and are regulated by heat (mutated lambda PR regulated by C1857; Jechlinger W, Szostak M P, Witte A, and Lubitz W. 1999 *FEMS Micro. Lett.* 173: 347-352), cold (lambda PR regulated by C1857 combined with lac or phage regulators, Jechlinger W, Szostak M P and Lubitz W. 1998 *Gene* 218: 1-7) or chemicals (lactose or IPTG with lacPO/Ptac or 3 MBZ with xylS repressor-PTol).

Plasmid release into the media would be induced by gene E expression. Addition of buffers directly to the media can be used to enhance release or selectivity. The cell mass would then be removed by filtration or centrifugation, leaving the plasmid in the clarified broth. Genomic DNA and RNA in the clarified broth can be reduced by use of a nuclease (either incorporated into the genome of the strain, and expressed in the cell line or exogenously added).

Alternatively, contaminant RNA and genomic DNA can be reduced utilizing existing known methods, such as selective denaturation or degradation by heat or alkali treatment of the clarified broth. In this case, removal of genomic DNA and RNA from the clarified culture would occur after ghosting rather than complete cell lysis, and release of cellular components such as LPS may be reduced. Plasmid release from cells can also be performed without a metal chelator, such as EDTA, to further reduce LPS shedding from ghosted cells. Compactation agents such as PEG or CTAB or divalent cations such as $CaCl_2$, can be utilized to selectively purify plasmid DNA from genomic and RNA contaminants. Such genomic DNA or RNA reduction methods are known in the art.

Alternatively, plasmid release could be delayed by inclusion of agents that alter membrane rigidity (e.g. 0.2 M $MgSO_4$) or increase DNA compaction (e.g. spermine) prior to or after gene E induction. The final cell population would be harvested, and buffer exchanged into a buffer that facilitates plasmid release (e.g. in case of $MgSO_4$, by reducing Mg concentration).

Example 16

Manufacture of Plasmid DNA Using Antibiotic Mediated Autolysis

An alternative autolysis method utilizes cell wall inhibiting antibiotics was evaluated. The T5RNase cassette in the pVEXBOmpAT5RNase construct was transferred to the pACYCB construct. Cultures of pACYCBT5RNase or pACYCBNative stuffer (control), each cotransformed with the gWizGFP plasmid, were grown in LB+50 ug/mL kanamycin+34 ug/mL chloramphenicol+4 mM $MgSO_4$, protein expression induced with arabinose to 0.2% final concentration for 1 hr at 30° C. during mid log growth and cell autolysis induced by addition of ampicillin and cefotaxim (Fluka) (B lactam antibiotics) to final concentrations of 100 and 10 ug/mL, respectively. Cultures were shaken overnight at 30° C. to effect lysis and nuclease digestion. Cell debris was removed by centrifugation and nucleic acid content in the supernatant evaluated by agarose gel (SYBR green II poststain) after phenol chloroform extraction to remove proteins. Genomic DNA was dramatically reduced in the T5RNase strain but not the control. Residual genomic DNA was removed by incubation (37° C. 30 min). No plasmid reduction was observed despite extended incubation of the lysed culture at elevated temperatures. As expected, the lysate viscosity was dramatically reduced with the T5RNase cell line compared to the control cell line.

These results demonstrate the general utility of the combination of plasmid-safe nucleases with various autolysis methods for plasmid production.

Thus, the reader will see that the plasmid-safe nucleases and associated production processes of the invention provide compositions and methods for improved plasmid production.

While the above description contains many specificities, these should not be construed as limitations on the invention, but rather as an exemplification of one preferred embodiment thereof. Many other variations are possible. For example genomic DNA reduction, utilizing endogenous exonucleases (recBCD), has been observed when chromosome breaks are induced using restriction endonucleases (Hanak and Ward, 2001) or gamma irradiation (MacPhee et. al., 1988); These ends are then the substrate for endogenous nucleases. In this format, the cells continue to grow after chromosome breaks are induced (overnight for irradiation). This works poorly when utilizing endogenous exonuclease activity to get rid of DNA, and might be greatly improved using the plasmid-safe endonucleases of the invention.

Accordingly, the scope of the invention should be determined not by the embodiments illustrated, but by the appended claims and their legal equivalents.

We claim:
1. A bacteria comprising:
    A) a chimeric nuclease comprising phage T5 D15 exonuclease and RNaseA; and
    B) a plasmid.
2. A method of making covalently closed super-coiled plasmid DNA comprising the steps of:
    A) introducing a nucleic acid sequence encoding a chimeric nuclease comprising phage T5 D15 exonuclease and RNaseA into *E. coli;*
    B) transfecting the *E. coli* with plasmid DNA;
    C) growing the transfected *E. coli;*
    D) expressing the chimeric nuclease in the periplasmic space of the *E. coli* such that genomic *E. coli* DNA is digested while the plasmid DNA is not digested; and

E) purifying the covalently closed super-coiled plasmid DNA.

\* \* \* \* \*